United States Patent
Park et al.

(10) Patent No.: US 8,916,525 B2
(45) Date of Patent: Dec. 23, 2014

(54) TNF-A AND TWEAK DUAL ANTAGONIST FOR THE PROPHYLAXIS AND TREATMENT OF AUTOIMMUNE DISEASES

(75) Inventors: Young Woo Park, Daejeon (KR); Ki Won Jo, Gyeonggi-do (KR); Srok Ho Yoo, Daejeon (KR); Jung Yu, Daejeon (KR); Dong Jin Kim, Daejeon (KR); Sun-Ha Yoon, Daejeon (KR); Eun Jung Song, Daejeon (KR); Eun Kyung Lee, Gyeonggi-do (KR); Jin Mi Oh, Gyeonggi-do (KR); Kyu Won Cho, Seoul (KR); Mi La Cho, Seoul (KR); Ho Youn Kim, Seoul (KR); Mi Kyung Park, Gyeonggi-do (KR); Hye Jwa Oh, Seoul (KR); Jin Sil Park, Seoul (KR); Yun Ju Woo, Seoul (KR); Jae Kyeong Byun, Chungcheongbuk-do (KR); Jun Geol Ryu, Gangwon-do (KR)

(73) Assignees: Korea Research Institute of Bioscience and Biotechnology, Taejeon-Si (KR); Industry-Academic Cooperation Foundation, The Catholic University of Korea, Seocho-Gu (KR)

( * ) Notice: Subject to any disclaimer, the term of this patent is extended or adjusted under 35 U.S.C. 154(b) by 0 days.

(21) Appl. No.: 13/635,868

(22) PCT Filed: Mar. 18, 2011

(86) PCT No.: PCT/KR2011/001900
§ 371 (c)(1),
(2), (4) Date: Sep. 18, 2012

(87) PCT Pub. No.: WO2011/115456
PCT Pub. Date: Sep. 22, 2011

(65) Prior Publication Data
US 2013/0017226 A1    Jan. 17, 2013

(30) Foreign Application Priority Data
Mar. 19, 2010 (KR) .................. 10-2010-0024699

(51) Int. Cl.
*A61K 38/17* (2006.01)
*A61P 17/00* (2006.01)
*A61P 19/02* (2006.01)
*A61P 19/04* (2006.01)
*A61P 21/00* (2006.01)
*A61P 25/00* (2006.01)
*A61P 3/10* (2006.01)
*A61P 7/06* (2006.01)
*C07K 14/525* (2006.01)
*C07K 14/705* (2006.01)

(52) U.S. Cl.
CPC ......... *C07K 14/525* (2013.01); *C07K 14/70575* (2013.01); *C07K 2319/32* (2013.01); *Y10S 514/814* (2013.01); *Y10S 514/886* (2013.01); *Y10S 514/903* (2013.01); *Y10S 514/885* (2013.01)
USPC .......... 514/18.9; 514/7.3; 514/16.6; 514/814; 514/886; 514/903; 514/885

(58) Field of Classification Search
None
See application file for complete search history.

(56) References Cited

U.S. PATENT DOCUMENTS

| 6,727,225 B2 * | 4/2004 | Wiley ........................ 424/134.1 |
| 2002/0110853 A1 | 8/2002 | Wiley |
| 2008/0175896 A1 | 7/2008 | Winkles et al. |

FOREIGN PATENT DOCUMENTS

| WO | WO 2004/003156 | 1/2004 |
| WO | WO 2006/043972 | 4/2006 |
| WO | WO 2007/009233 | 1/2007 |
| WO | WO 2010/003108 | 1/2010 |
| WO | WO 2010/003118 | 1/2010 |

\* cited by examiner

*Primary Examiner* — David Romeo
(74) *Attorney, Agent, or Firm* — Lathrop & Gage LLP

(57) ABSTRACT

The present invention relates to TNFR2-TWEAKR fusion protein, more precisely to TNFR2-TWEAKR fusion protein acting as a double-antagonist to TNF-α and TWEAK, known as major causes of autoimmune arthritis which is one of autoimmune diseases. When the composition comprising TNFR2-TWEAKR fusion protein was treated to Th17 cells, the secretion of the inflammatory cytokine IL-17 was reduced but the secretion of the anti-inflammatory cytokine IL-10 generated in Treg cells was increased. Such effect of TNFR2-TWEAKR fusion protein was far greater than that of a single protein such as TNFR2-Fc or TWEAK-Fc. The TNFR2-TWEAKR fusion protein of the present invention has not only excellent treatment effect on arthritis in CIA mouse model not also excellent treatment effect on autoimmune rheumatoid arthritis by increasing the expression of Treg, the immune suppressive cells. Therefore, the TNFR2-TWEAKR fusion protein of the present invention can be effectively used as an active ingredient for the composition for the prevention and treatment of autoimmune disease.

2 Claims, 18 Drawing Sheets

A.

B.

TNF-A AND TWEAK DUAL ANTAGONIST FOR THE PROPHYLAXIS AND TREATMENT OF AUTOIMMUNE DISEASES

CROSS-REFERENCES TO RELATED APPLICATION

This patent application is a U.S. national phase under 35 U.S.C 371 of PCT/KR2011/001900 filed on Mar. 18, 2011, which claims the benefit of priority from Korean Patent Applications No. 10-2010-0024699, filed on Mar. 19, 2010, the contents of which are incorporated herein by reference in its entirety.

REFERENCE TO SEQUENCE LISTING

A sequence listing containing SEQ ID NOS: 1-19 is submitted herewith and is specifically incorporated by reference.

BACKGROUND OF THE INVENTION

1. Field of the Invention

The present invention relates to a composition for the prevention and treatment of autoimmune diseases comprising a double antagonist to TNF-α and TWEAK as an active ingredient.

2. Description of the Related Art

Immune system plays a role in protecting human body from antigens, the harmful foreign materials. Such antigens are exemplified by bacteria, viruses, toxic materials, cancer cells, and blood or tissues of other people or animals. Immune system produces antibodies to destroy such harmful foreign materials introduced. However, if immune system is malfunctioning, the system cannot distinguish normal health organs of its own from harmful foreign antigens, and thus it destroys normal tissues as well. This reaction is called autoimmune disease. Such reaction shows allergic hypersensitivity reaction. Allergy is the reaction against foreign materials that are not harmful for human body, but in the case of autoimmune disease, reaction target includes normal tissues. The reason why immune system cannot distinguish normal organs from antigens is not known. There is only assumed theory that microorganisms such as bacteria or drugs might cause such disease in those who are inherited specifically with such genes that are vulnerable to autoimmune disease.

Autoimmune disease is exemplified by Hashimoto's thyroiditis, pernicious anemia, Addison's disease, type 1 diabetes, autoimmune rheumatoid arthritis, Systemic lupus erythematosus, dermatomyositis, Sjogren syndrome, Lupus erythematosus, Multiple sclerosis, Myasthenia gravis, Reactive arthritis, Grave's disease, and Celiac disease—sprue, etc.

The purpose of the treatment of autoimmune disease is to regulate autoimmune response and to recover damaged immune function. The treatment method can be varied from the type of autoimmune disease. For example, if there is a problem in blood, blood transfusion is required. If any abnormality is observed in bone, joint, or muscle, physical exercise or other functional treatment is required. In addition, drug is prescribed in order to regulate immune response. Such drug is called immunosuppressive medicine, which is exemplified by corticosteroids such as prednisone and nonsteroids such as cyclophosphamide, azathioprine, and tacrolimus, etc.

Even though 21 million people world-widely, which are approximately 1% of the total population on earth, catch rheumatoid arthritis (RA), one of autoimmune disease, the reason of this disease has not been disclosed, yet. The symptom of rheumatoid arthritis is symmetric systemic chronic inflammation in diarthrodial joint. When it gets worse, even joint dysfunction occurs. Make matter worse, such mal-functioning of autoimmune system brings inflammation and pain not only in joint but also in other tissues around joint and further in other organs of entire body including lung, skin, and eye with causing pain and osteoporosis, resulting in severe decrease of life-quality making normal daily life impossible.

The previous treatment of rheumatoid arthritis focused on delaying the development of the disease or alleviating the accompanied pain by the improvement of life habit, surgical operation, and administration of a therapeutic agent, with inhibiting infection but without expecting any improvement of joint functions. However, the recent treatment is aiming at the full recovery of joint function. This has been made possible by the development of anti-TNF antagonists, which has been regarded the most dramatic discovery for the treatment of rheumatoid arthritis.

Tumor necrosis factor (TNF) is the pleiotropic cytokine, which plays an important role not only in inflammatory reaction but also in immune system. It is found in the joint of rheumatoid arthritis patient and colon of Crohn's disease patient. It has also been reported that tumor necrosis factor plays an important role in bone destruction, too. Therefore, all the treatment agents have been developed in order to inhibit TNF activity, precisely to interrupt signal transduction by binding to ligand belonging to TNF superfamily or to interrupt the bond between TNF ligand and receptor. To inhibit TNF signal transduction, monoclonal antibody against TNF ligand or recombinant protein has been used. Precisely, the treatment method using monoclonal antibody such as infliximab (Remicade) or adalimumab (Humira) has been used. And the treatment method using recombinant protein such as CTLA-41 g or entracept (Enbrel) has been also used. More precisely, infliximab is a chimera antibody comprising murine variable region and human IgG1 and κ constant region, which neutralizes the biological activity of TNF by binding to soluble, transmembrane TNF to inhibit the conjugation between TNF and its receptor. The structure of infliximab is similar to that of the natural antibody. Entracept is a fusion protein composed of extracellular domain of p75 TNF receptor and human IgG1 hinge and Fc domain. Infliximab, entracept, and adalimumab are the biological agents first accredited as rheumatoid arthritis treatment agents, which have been used for the past 10 years showing high efficiency. In addition to TNF, other cytokines have been targeted to develop a treatment agent. As DMARD (disease-modifying anti-rheumatic drugs) inhibiting interleukin, treatment agents have been developed targeting IL-6 or IL-1. However, the treatment effect is not as good as those of the anti-TNF agents.

TWEAK (TNF-related weak inducer of apoptosis) is an apoptosis inducer, which is a kind of ligands belonging to TNF superfamily. TWEAK is a cytokine that regulates a variety of cellular responses including anti-inflammatory response, angiogenesis, and cell division, etc. It was confirmed that inflammation in joint, angiogenesis in synovial membrane, and erosion of joint and bone were reduced, when TWEAK antibody was treated in CIA (collagen-induced arthritis) animal model before the development of the disease in order to inhibit TWEAK signal transduction (*J. Immunol.* 2006 Aug. 15; 177(4): 2610-20).

Despite the excellent treatment effect, the anti-TNF agents have many problems to overcome. One example is the side effect of the administration of anti-TNF agents, which is that TNF mechanism is stopped working, leading to mal-functioning of immune system with increasing risk of fungal or viral infection. Particularly, the chance of recurrence of dormant tuberculosis increases. In addition, demyelinating disorder such as multiple sclerosis or hematologic malignancies might be caused. According to rheumatoid society, chances of skin cancer development are higher in rheumatoid arthritis patients administered with anti-TNF agents than in those treated with the conventional therapeutic agents.

The treatment effect of the agent is not all the same among rheumatoid arthritis patients. Two thirds of the patients showed treatment effect, but one third of the patients were not improved. This result indicates that the treatment is limited by the medical history or genetic factors. Not only the pain from the disease but also the side effects accompanied by the treatment and the safety problems have to be considered and overcome. In the case of pregnant women having rheumatoid arthritis, the safety of fetus has been an issue when anti-TNF agent is administered. Scientists are faced with the task of developing diagnostic method to predict the treatment effect and the side effects thereby.

The present inventors tried to develop a novel therapeutic agent for autoimmune disease which is advantageous in overcoming the limitation of efficiency and safety matter of the conventional single antagonist used as an anti-TNF treatment agent. As a result, the inventors constructed TNFR2-TWEAKR fusion protein having antagonism against TNF-alpha (α) and TWEAK. The inventors further confirmed that when TNFR2-TWEAKR was treated to Th17 cells, the secretion of IL-17, the inflammatory cytokine, and the expression of RORc were all reduced, suggesting that TNFR2-TWEAKR had inhibitory effect on the secretion of inflammatory cytokine. At the same time, the inventors also confirmed that TNFR2-TWEAKR treatment resulted in up-regulation of IL-10, the anti-inflammatory cytokine secreted in autoimmune protective cells. In addition, RANKL, known to be involved in osteoclast, was also up-regulated in consistent with up-regulation of TWEAK in the serum of autoimmune arthritis patient. In CIA mouse model, the TNFR2-TWEAKR fusion protein of the present invention was confirmed to have not only the treatment effect on arthritis but also the treatment effect on autoimmune arthritis by increasing the expression of Tregs, the immune suppressive cells. Thus, the present inventors completed this invention by confirming the possibility of the TNFR2-TWEAKR fusion protein of the present invention as a novel treatment agent for autoimmune disease.

SUMMARY OF THE INVENTION

It is an object of the present invention to provide TNF-α (alpha) and TWEAK fusion protein as well as a composition for the prevention and treatment of autoimmune disease comprising the same as an active ingredient.

To achieve the above object, the present invention provides a fusion protein in which the fragment containing TNFR2 (tumor necrosis factor receptor type 2) protein or extracellular domain of the said TNFR2 is linked to the fragment containing TWEAKR (TNF-related weak inducer of apoptosis receptor) or extracellular domain of the said TWEAKR.

The present invention also provides a polynucleotide encoding the TNFR2-TWEAKR fusion protein.

The present invention further provides an expression vector containing the polynucleotide encoding the TNFR2-TWEAKR fusion protein.

The present invention also provides a transformant obtained by transfecting host cells with the expression vector comprising the polynucleotide encoding the TNFR2-TWEAKR fusion protein.

The present invention also provides a composition for the prevention and treatment of autoimmune disease comprising the TNFR2-TWEAKR fusion protein as an active ingredient.

The present invention also provides a method for the treatment of autoimmune disease containing the step of administering pharmaceutically effective dose of the TNFR2-TWEAKR fusion protein to a subject having autoimmune disease.

The present invention also provides a method for the prevention of autoimmune disease containing the step of administering pharmaceutically effective dose of the TNFR2-TWEAKR fusion protein to a subject.

In addition, the present invention provides the TNFR2-TWEAKR fusion protein for the prevention and treatment of autoimmune disease.

ADVANTAGEOUS EFFECT

As explained hereinbefore, the present invention relates to a composition comprising TNFR2-TWEAKR fusion protein characterized by antagonism against TNFR2 and TWEAK, which have presumed to be major causes for autoimmune rheumatoid arthritis, one of autoimmune diseases. The TNFR2-TWEAKR fusion protein inhibited the secretion of IL-17, the inflammatory cytokine, better than the conventional TNFR2-Fc or TWEAKR-Fc and increased the secretion of IL-10, the anti-inflammatory cytokine, better than TNFR2-Fc and TWEAKR-Fc. Besides, the TNFR2-TWEAKR fusion protein showed excellent alleviating effect on infiltration, inflammation, and cartilage destruction in joint in CIA mouse model. The fusion protein of the present invention was also proved to increase the expression of Treg cells, the immune suppressive cells, to bring the treatment effect on autoimmune rheumatoid arthritis. Therefore, the TNFR2-TWEAKR fusion protein of the present invention can be effectively used as an active ingredient for the composition having the preventive and therapeutic effect on autoimmune diseases.

BRIEF DESCRIPTION OF THE DRAWINGS

The application of the preferred embodiments of the present invention is best understood with reference to the accompanying drawings, wherein.

BSA: bovine serum albumin used as the control;

F228: the product prepared by using TWEAKR F228 primer; and

F448: the product prepared by using TWEAKR F448 primer.

Figure 3:
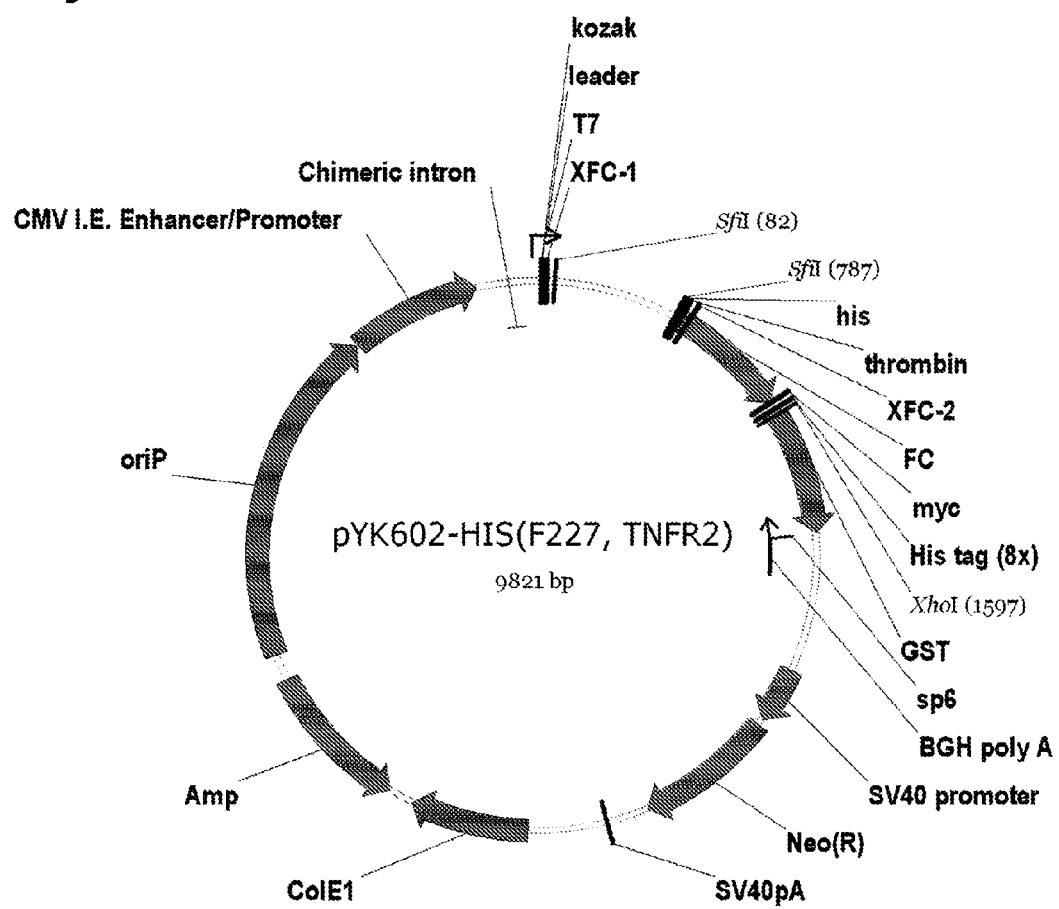

FIG. 3 is a diagram illustrating the structure of TNFR2 in which TNFR2 gene has been cloned in the expression vector pYK602-HIS-Fc.

Figure 4:
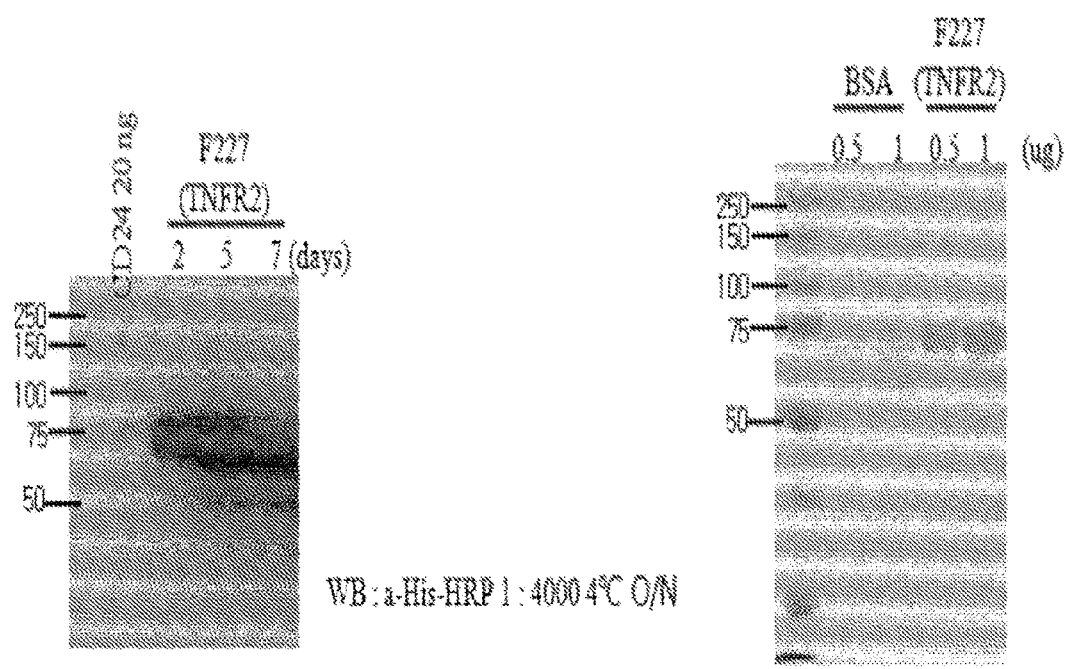

FIG. 4 is a set of photographs illustrating the result of western blot confirming the expression of TNFR2 cloned in the expression vector pYK602-HIS-Fc, and the result of another western blot using HIS antibody performed after purifying the expressed protein by using protein A beads:

BSA: bovine serum albumin used as the control; and

F227: the product prepared by using TWEAKR F227 primer.

Figure 5:
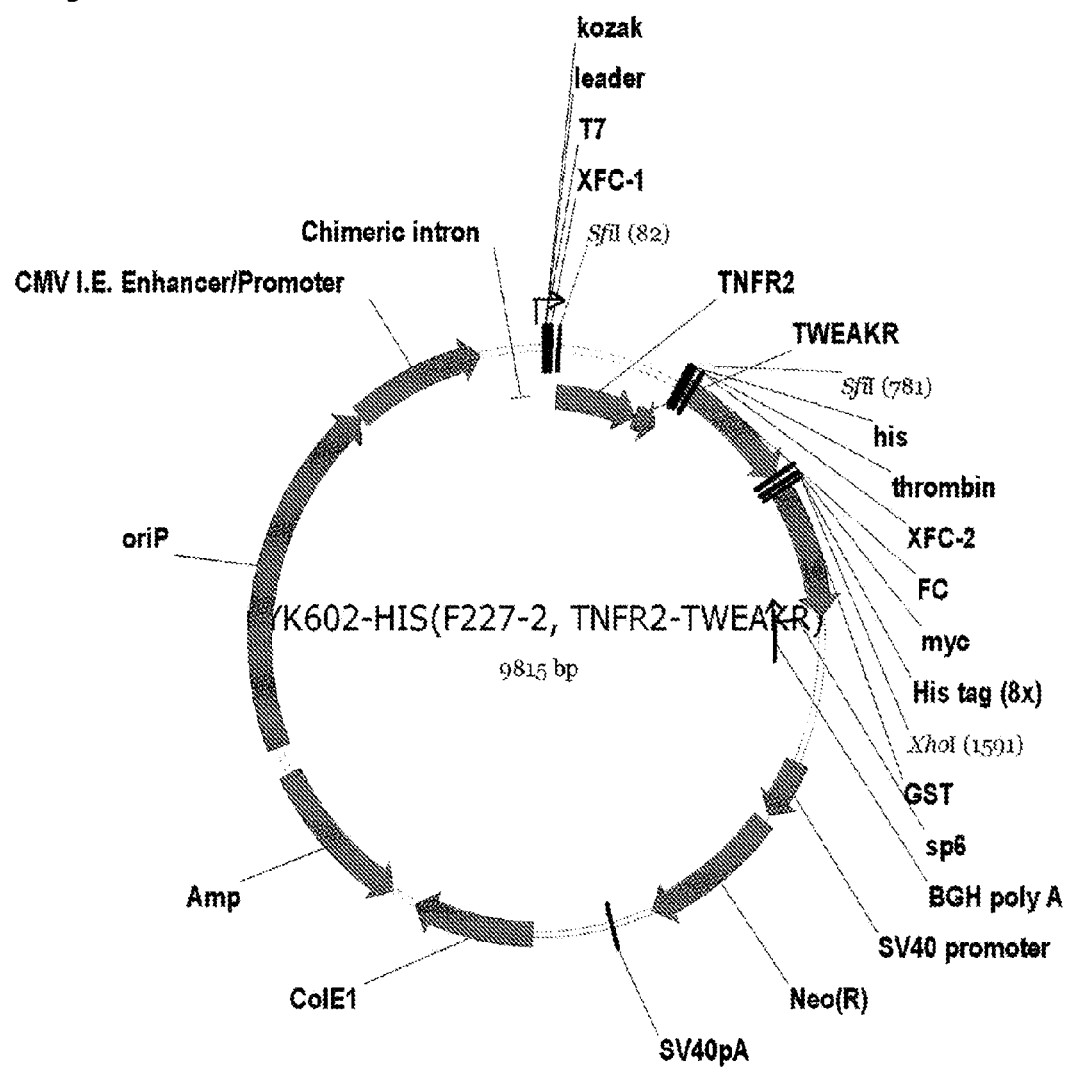

FIG. 5 is a diagram illustrating the structure of TNFR2-TWEAKR fusion protein prepared by cloning TNFR2 gene together with TWEAKR gene in the expression vector pYK602-HIS-Fc.

Figure 6:
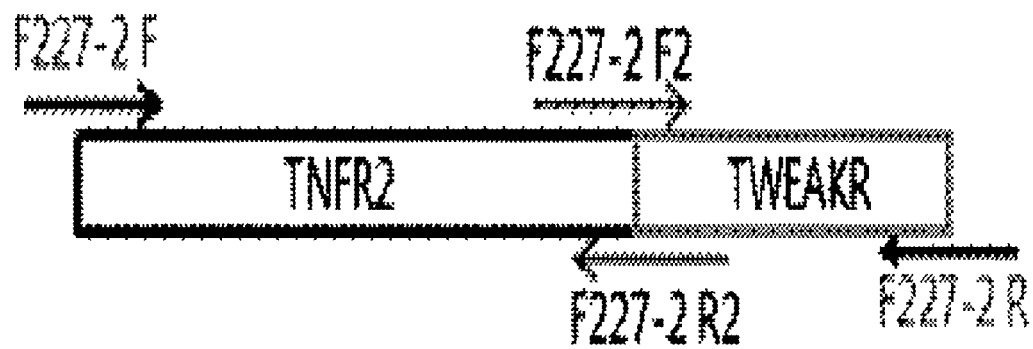

FIG. 6 is a diagram illustrating the structure of PCR primer used for the construction of TNFR2-TWEAKR fusion protein.

Figure 7:
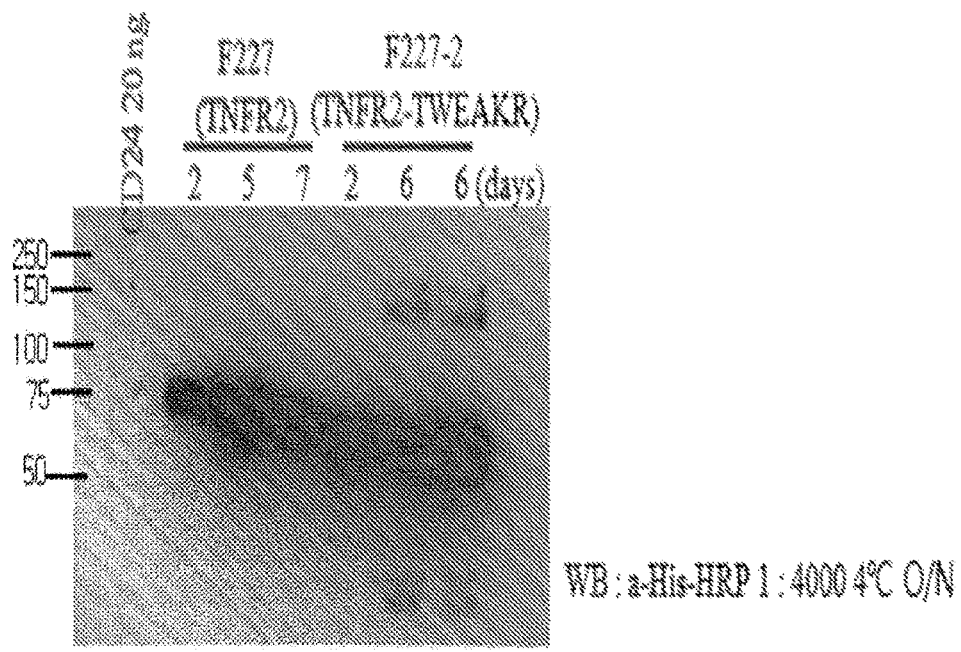

FIG. 7 is a photograph illustrating the result of western blot confirming the expression of TNFR2-TWEAKR fusion protein cloned in the expression vector pYK602-HIS-Fc:
CD24: control;
F227: the product prepared by using TNFR2F227 primer; and
F227-2: the product prepared by using F227-2 primer for the construction of TNFR2-TWEAKR fusion protein.

Figure 8:
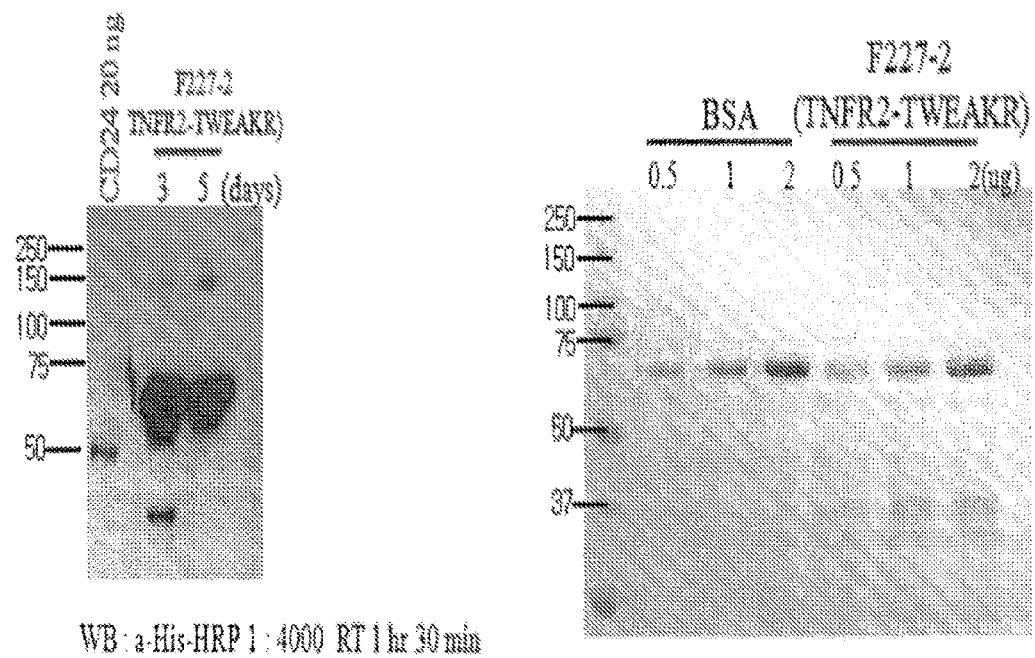

FIG. 8 is a set of photographs illustrating the result of western blot confirming the expression of TTNFR2-TWEAKR fusion protein cloned in the expression vector pYK602-HIS-Fc, and the result of another western blot using HIS antibody performed after purifying the expressed TNFR2-TWEAKR fusion protein by using protein A beads:
CD24: control; and
F227-2: the product prepared by using F227-2 primer for the construction of TNFR2-TWEAKR fusion protein.

Figure 9:
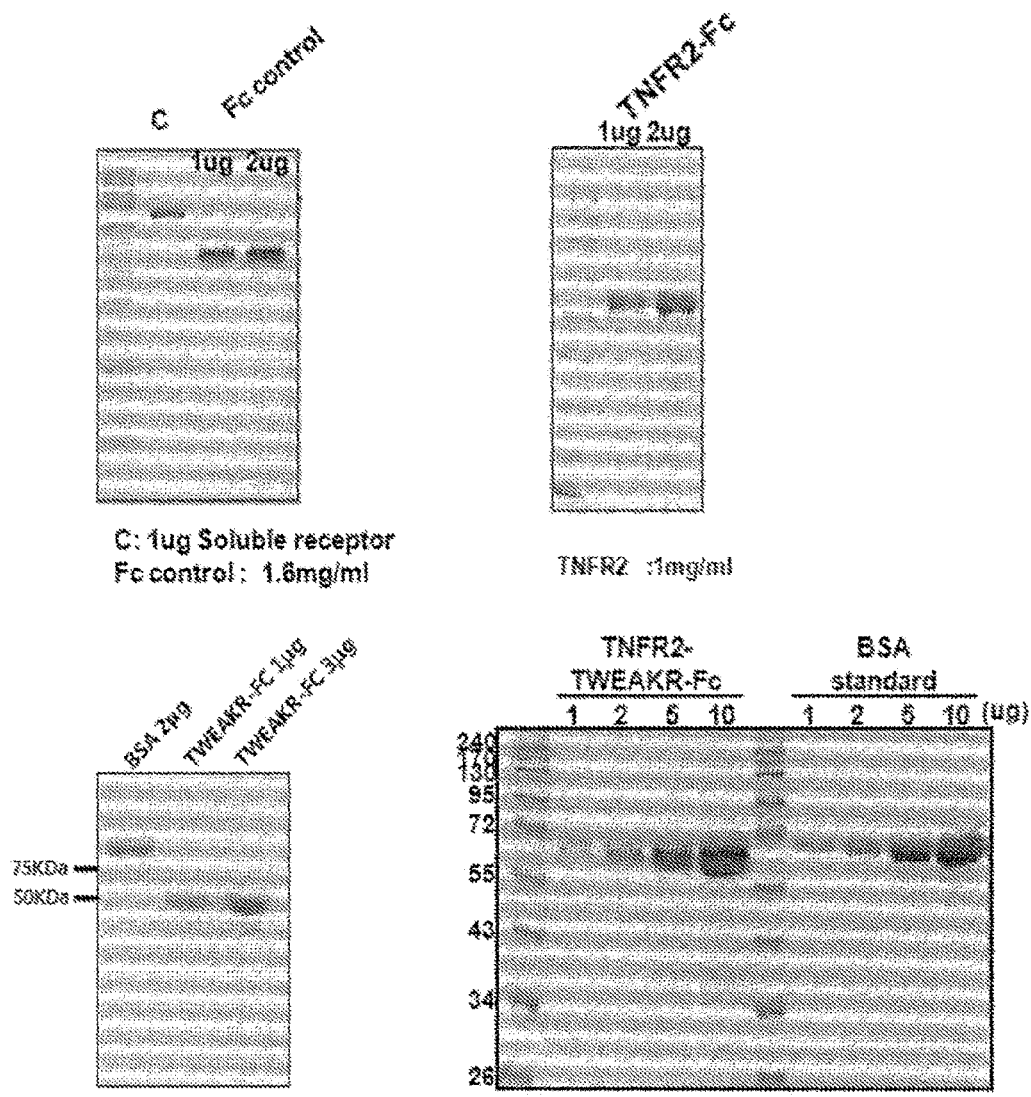

FIG. 9 is a set of photographs illustrating the result of western blot showing the result of mass-purification of TNFR2-TWEAKR fusion protein:
Fc control: vector control including Fc domain;
TNFR2-Fc: TNFR2 expression group including Fc domain;
TWEAKR-Fc: TWEAKR expression group including Fc domain;
TNFR2-TWEAKR fusion protein: TNFR2-TWEAKR fusion protein expression group including Fc domain; and
BSA: bovine serum albumin used as the control.

Figure 10:
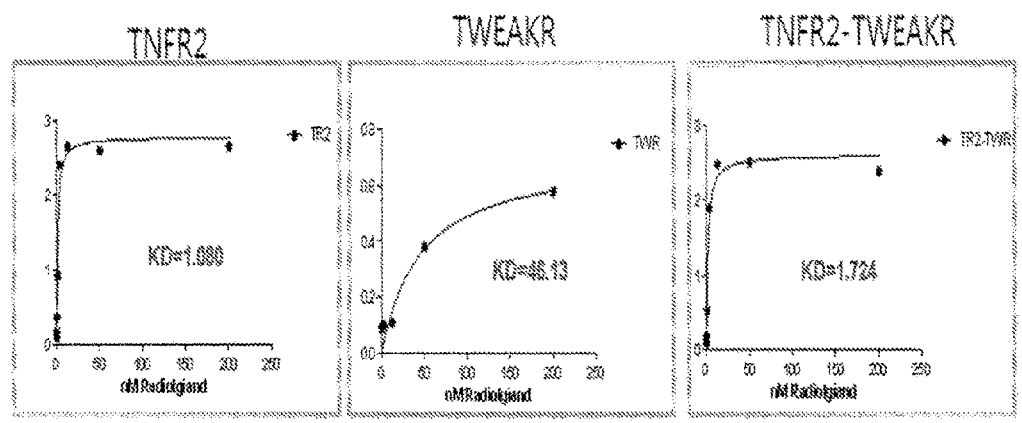
Figure 10:
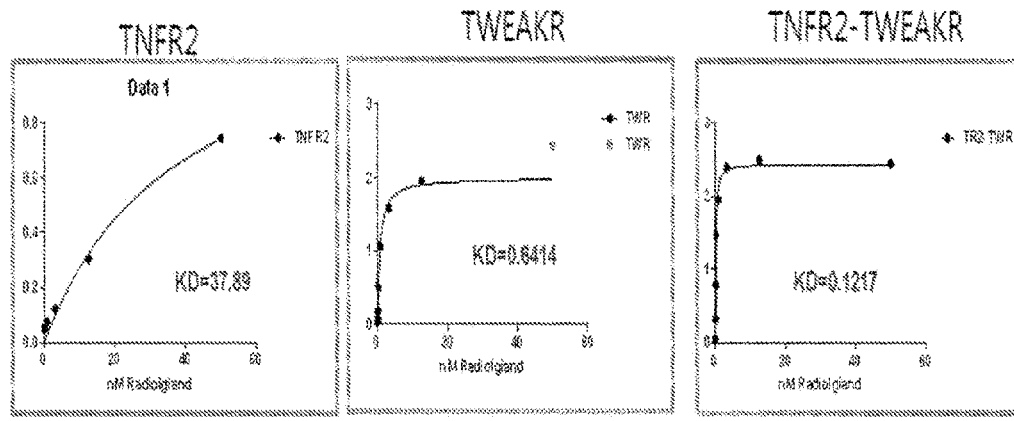

FIG. 10 is a set of graphs illustrating the binding affinity between TNFR2-TWEAKR fusion protein and its ligand TNF-α and TWEAK.

Figure 11:
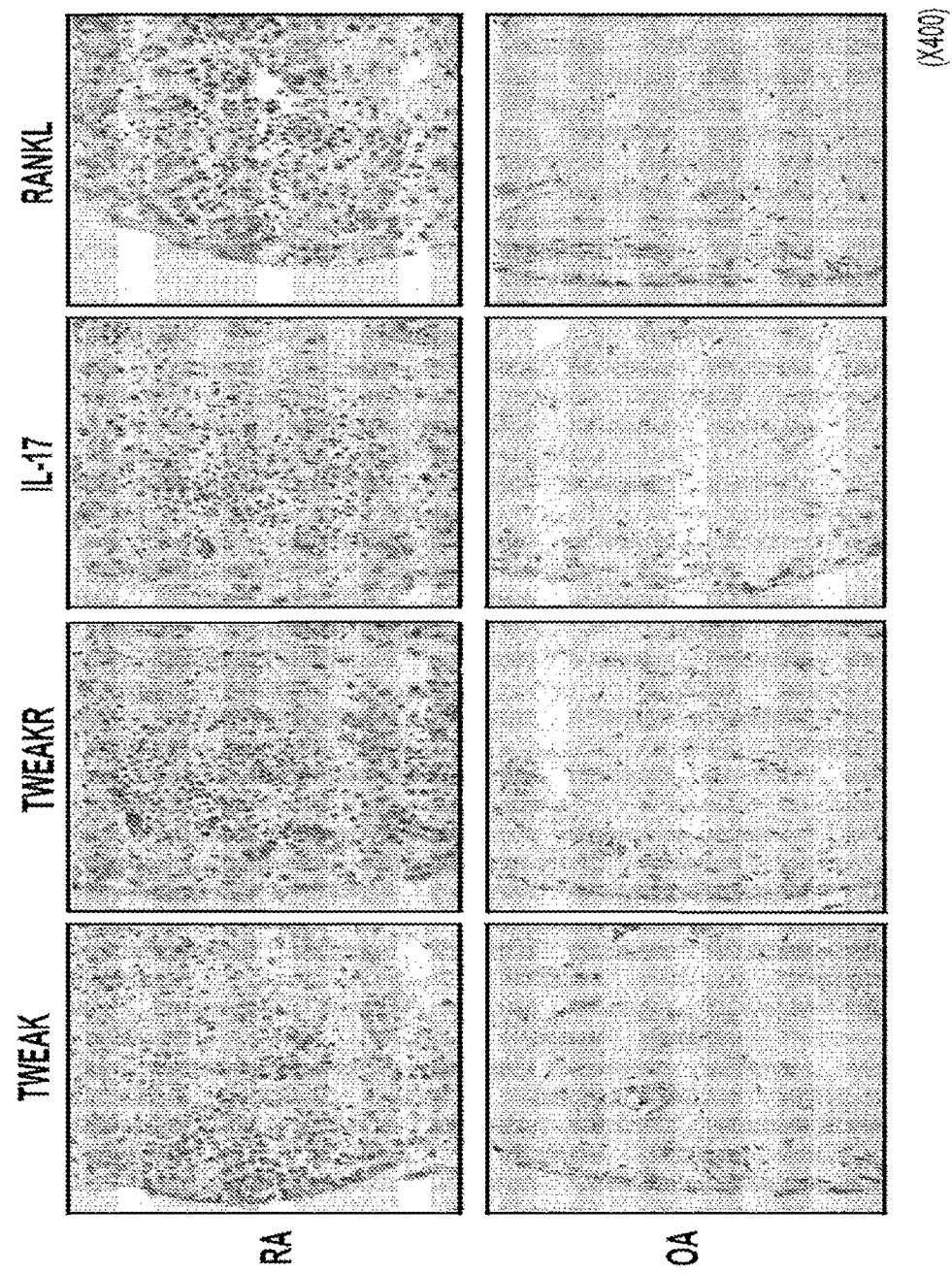

FIG. 11 is a set of photographs illustrating the expressions of TWEAK, TWEAKR, IL-17, and RANKL in synovial membrane tissue of autoimmune arthritis patient.

Figure 12:
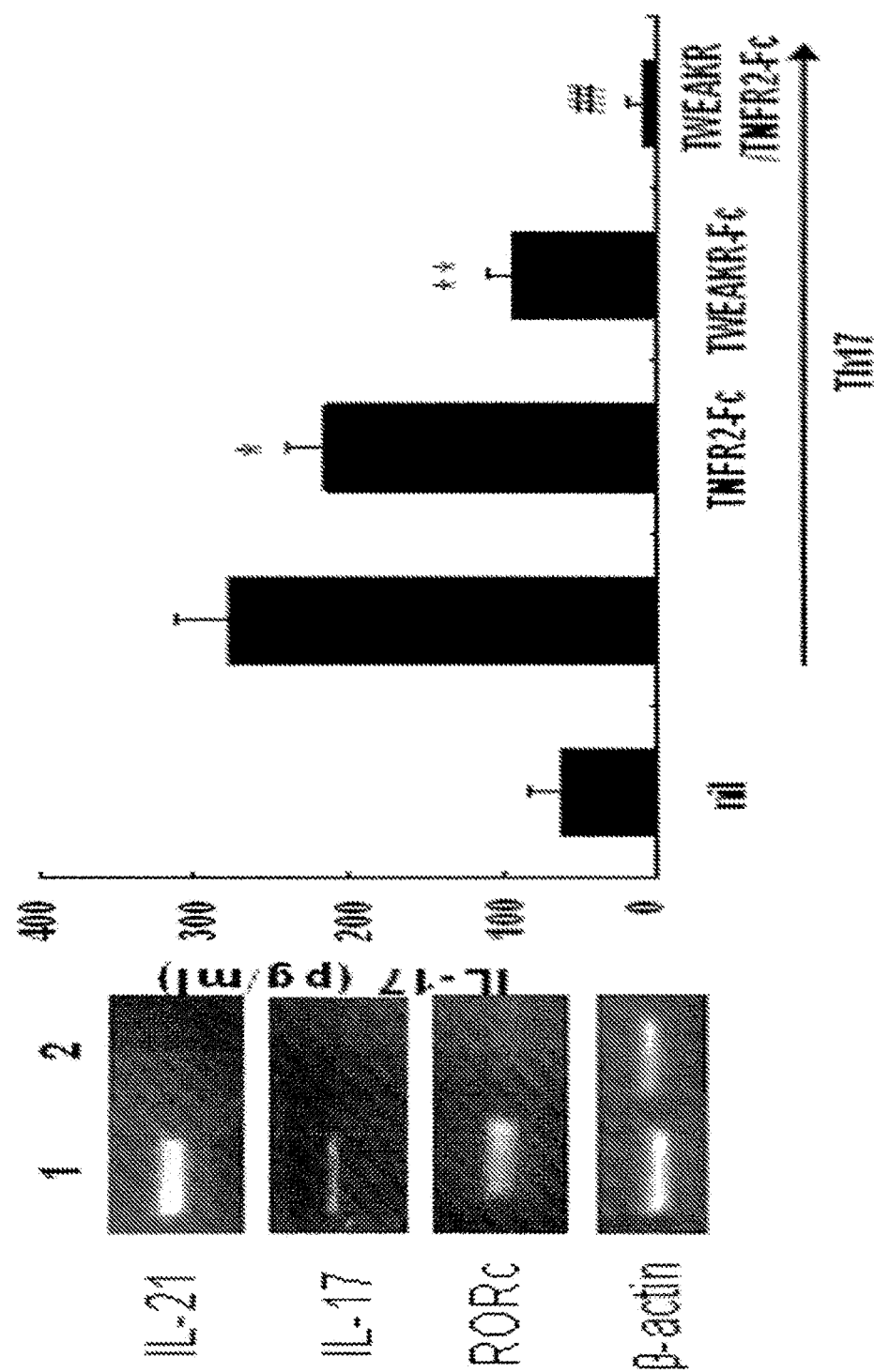

FIG. 12 is a set of photographs and a graph illustrating the result of RT-PCR confirming the expressions of IL-21, IL-17, RORc, and β-actin in Th17 cells treated with TNFR2-TWEAKR fusion protein, and also illustrating the quantification of the inflammatory cytokine IL-17 secreted in the Th17-polarizing condition treated with TNFR2, TWEAKR-Fc, and TNFR2-TWEAKR fusion protein, respectively.

Figure 13:
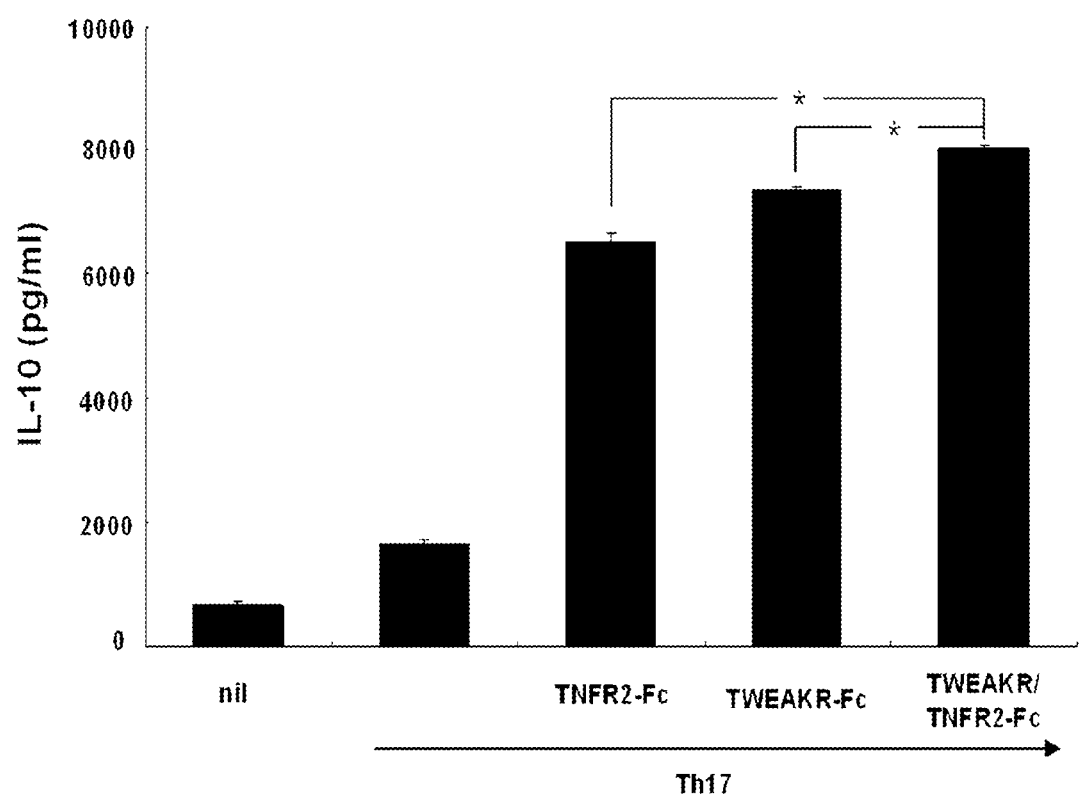

FIG. 13 is a graph illustrating the amount of the anti-inflammatory cytokine IL-10 secreted in the Th17-polarizing condition treated TNFR2-TWEAKR fusion protein.

Figure 14:
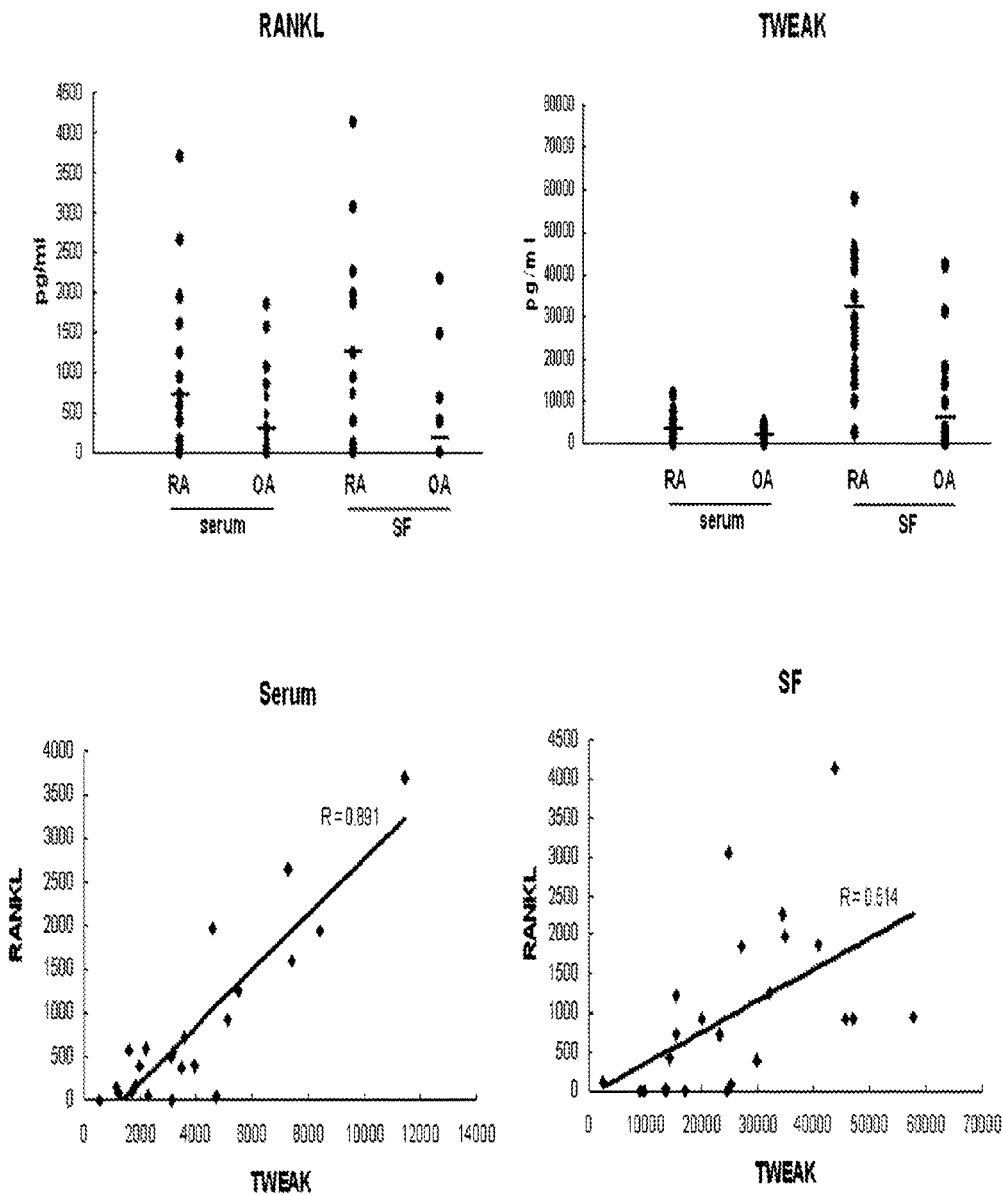

FIG. 14 is a set of graphs illustrating the quantification of TWEAK and RANKL in serum and synovial fluid of autoimmune arthritis patient.

Figure 15:
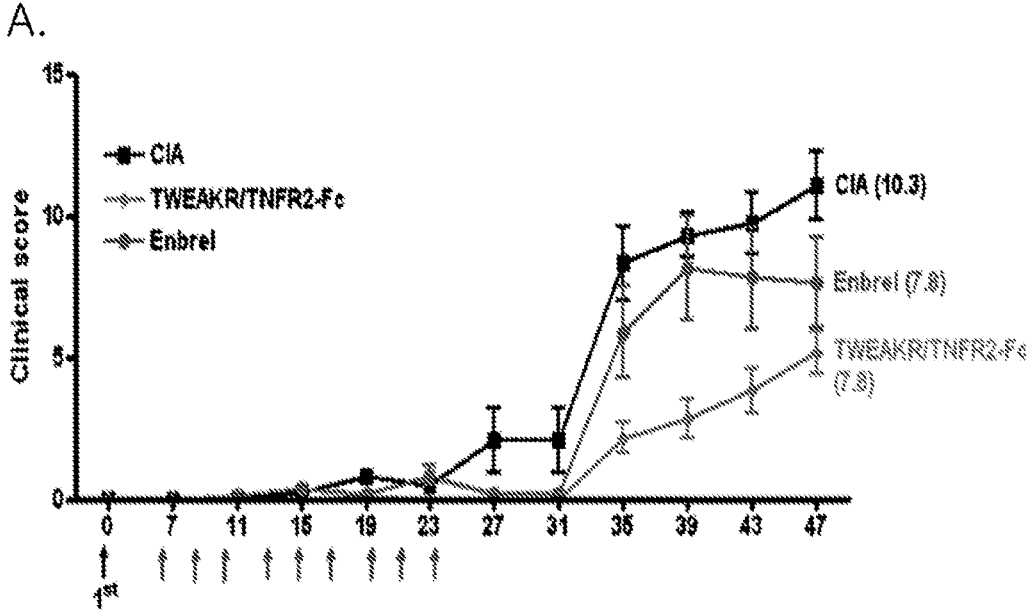
Figure 15:
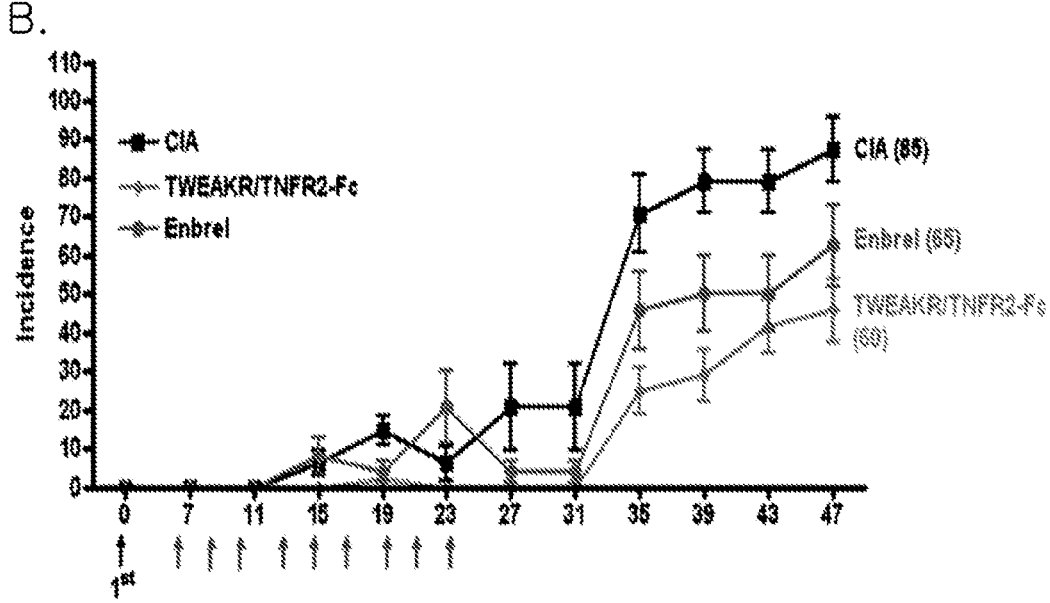

FIG. 15 is a set of graphs illustrating the treatment effect of the TNFR2-TWEAKR fusion protein of the present invention on arthritis in CIA mouse model:

FIG. 15A is a graph illustrating the Clinical Score observed after the administration of the TNFR2-TWEAKR fusion protein of the present invention or Enbrel to CIA mouse model;
↑: the time of administration of TNFR2-TWEAKR fusion protein or Enbrel;
CIA: negative control—CIA (collagen induced arthritis) animal model group treated with nothing;
TNFR2-TWEAKR-Fc: CIA animal model group treated with TNFR2-TWEAKR fusion protein;
Enbrel: CIA animal model group treated with the arthritis treatment agent Enbrel;

FIG. 15B is a graph illustrating the Incidence observed after the administration of the TNFR2-TWEAKR fusion protein of the present invention or Enbrel to CIA mouse model;
↑: the time of administration of TNFR2-TWEAKR fusion protein or Enbrel;
CIA: negative control—CIA (collagen induced arthritis) animal model group treated with nothing;
TNFR2-TWEAKR-Fc: CIA animal model group treated with TNFR2-TWEAKR fusion protein; and
Enbrel: CIA animal model group treated with the arthritis treatment agent Enbrel.

Figure 16:
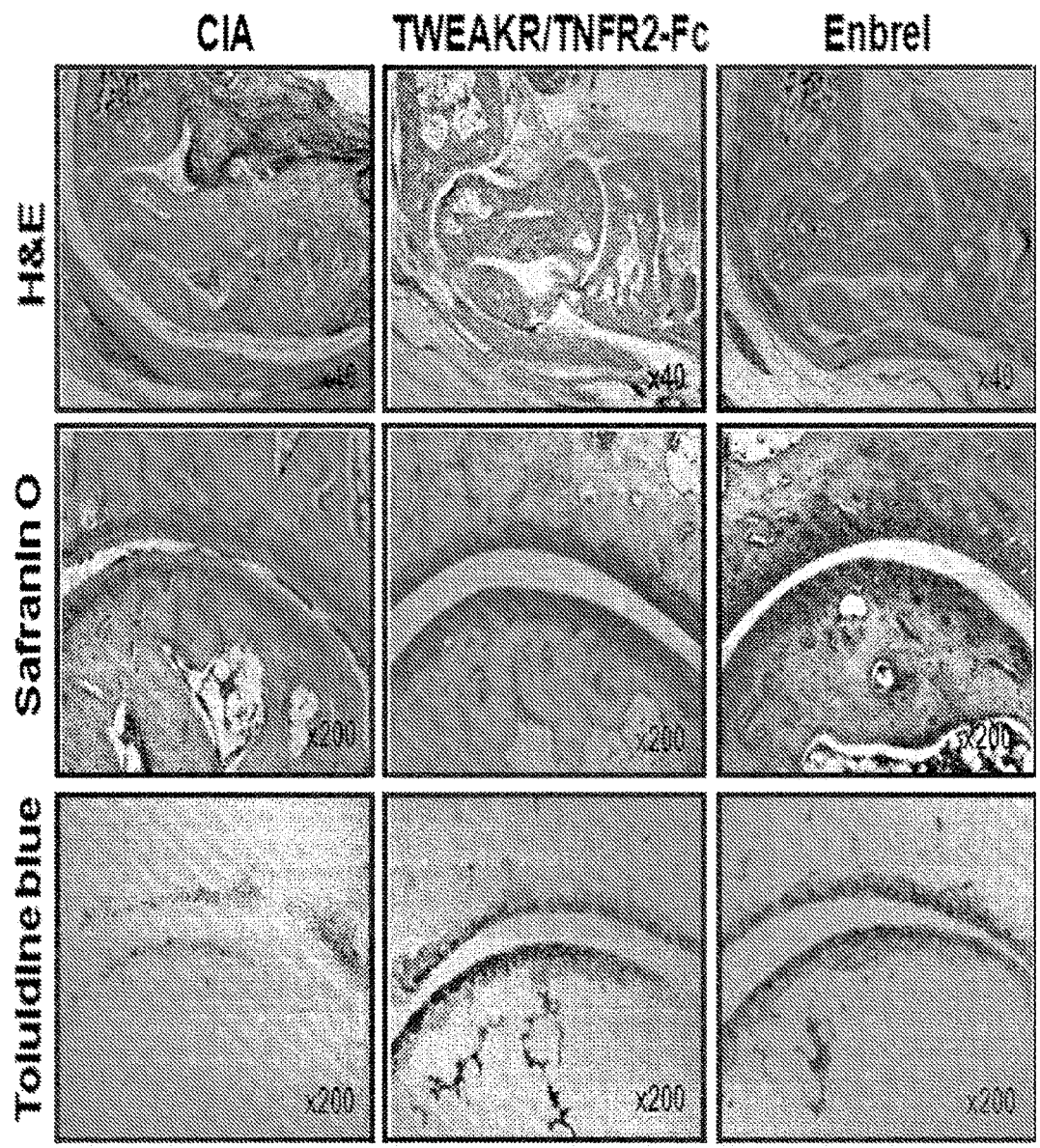

FIG. 16 is a set of photographs illustrating the arthritis alleviating effect of TNFR2-TWEAKR fusion protein in CIA mouse model, confirmed by immunohistochemical staining method:
CIA: negative control—CIA (collagen induced arthritis) animal model group treated with nothing;
TNFR2-TWEAKR-Fc: CIA animal model group treated with TNFR2-TWEAKR fusion protein; and
Enbrel: CIA animal model group treated with the arthritis treatment agent Enbrel.

Figure 17:
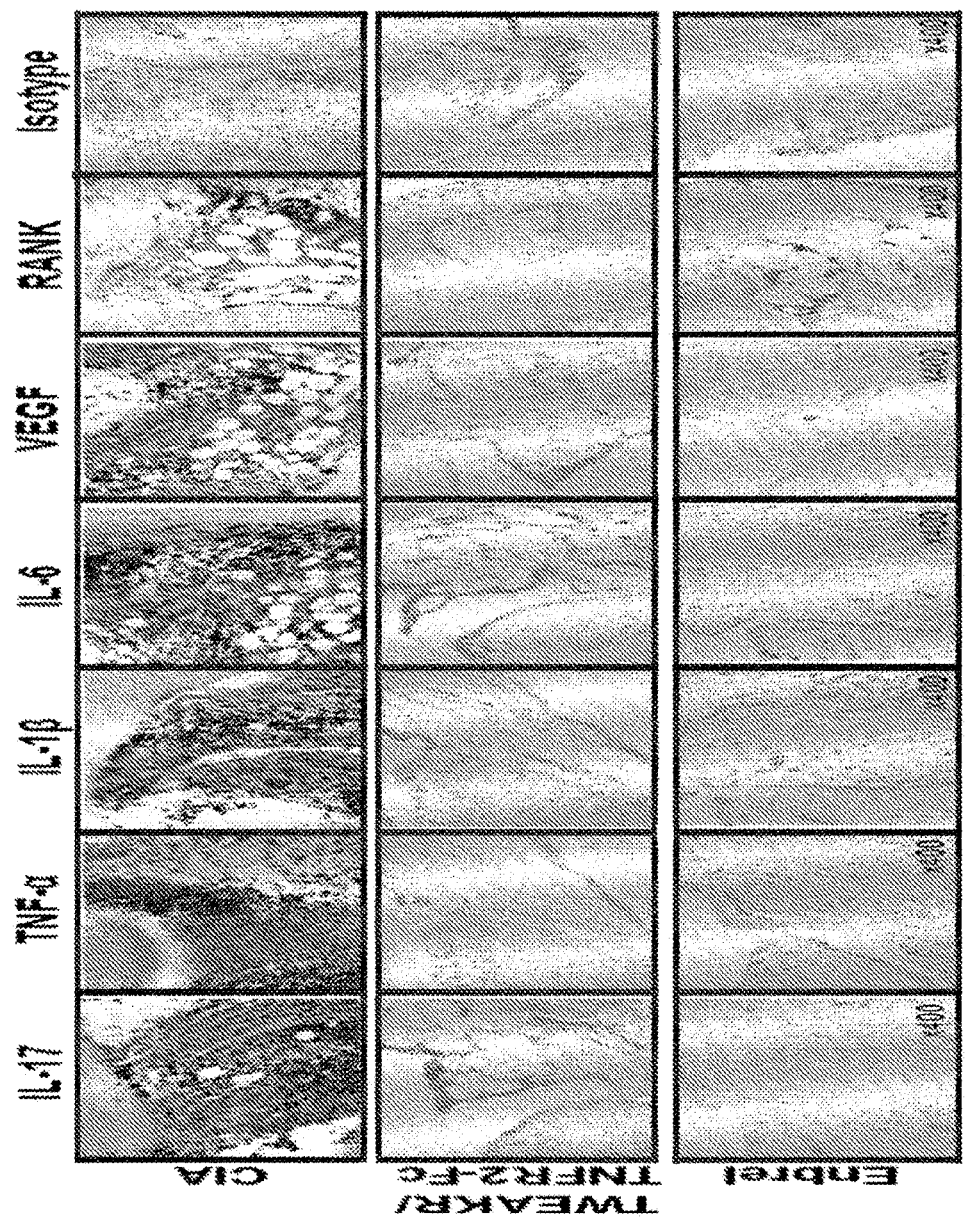

FIG. 17 is a set of photographs illustrating the anti-inflammatory effect of TNFR2-TWEAKR fusion protein in CIA mouse model, confirmed by immunohistochemical staining method:
CIA: negative control—CIA (collagen induced arthritis) animal model group treated with nothing;
TNFR2-TWEAKR-Fc: CIA animal model group treated with TNFR2-TWEAKR fusion protein; and
Enbrel: CIA animal model group treated with the arthritis treatment agent Enbrel.

Figure 18:
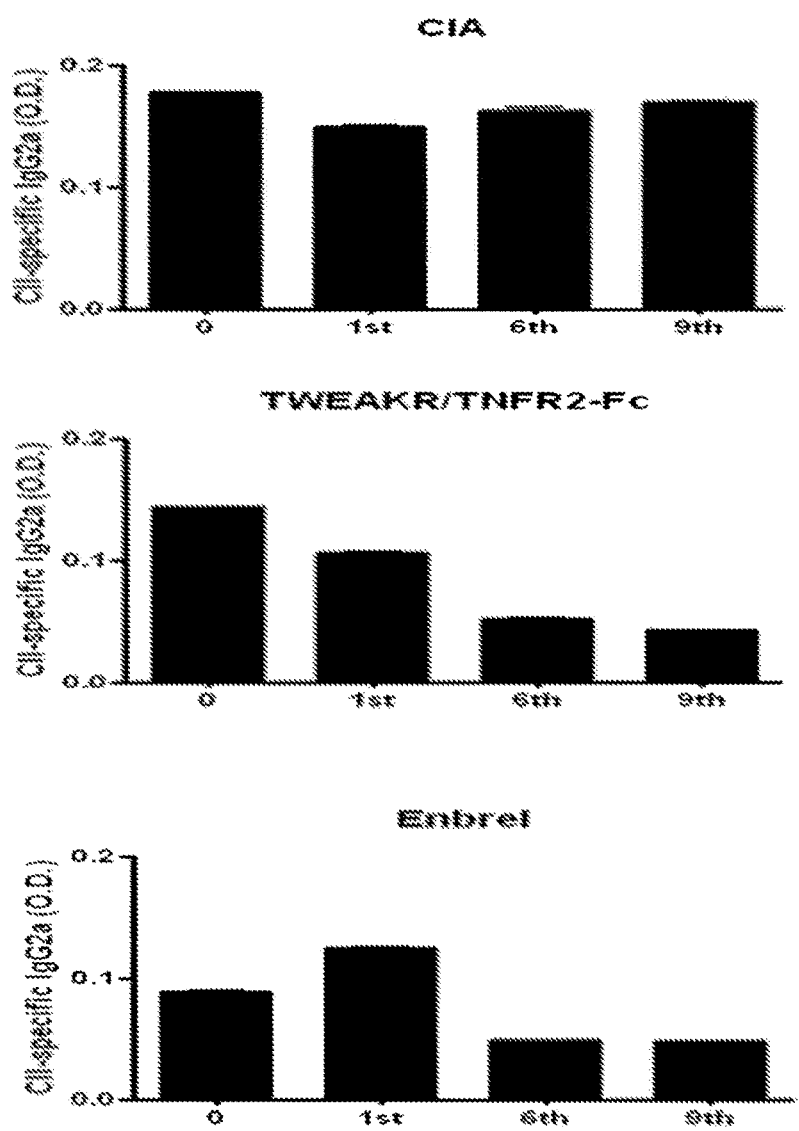

FIG. 18 is a set of graphs illustrating the CII specific IgG2a production in CIA mouse model:
0: before the administration of TNFR2-TWEAKR fusion protein or Enbrel;
1st: first administration of TNFR2-TWEAKR fusion protein or Enbrel;
6th: sixth administration of TNFR2-TWEAKR fusion protein or Enbrel;
9th: ninth administration of TNFR2-TWEAKR fusion protein or Enbrel;
CIA: negative control—CIA (collagen induced arthritis) animal model group treated with nothing;
TNFR2-TWEAKR-Fc: CIA animal model group treated with TNFR2-TWEAKR fusion protein; and
Enbrel: CIA animal model group treated with the arthritis treatment agent Enbrel.

Figure 19:
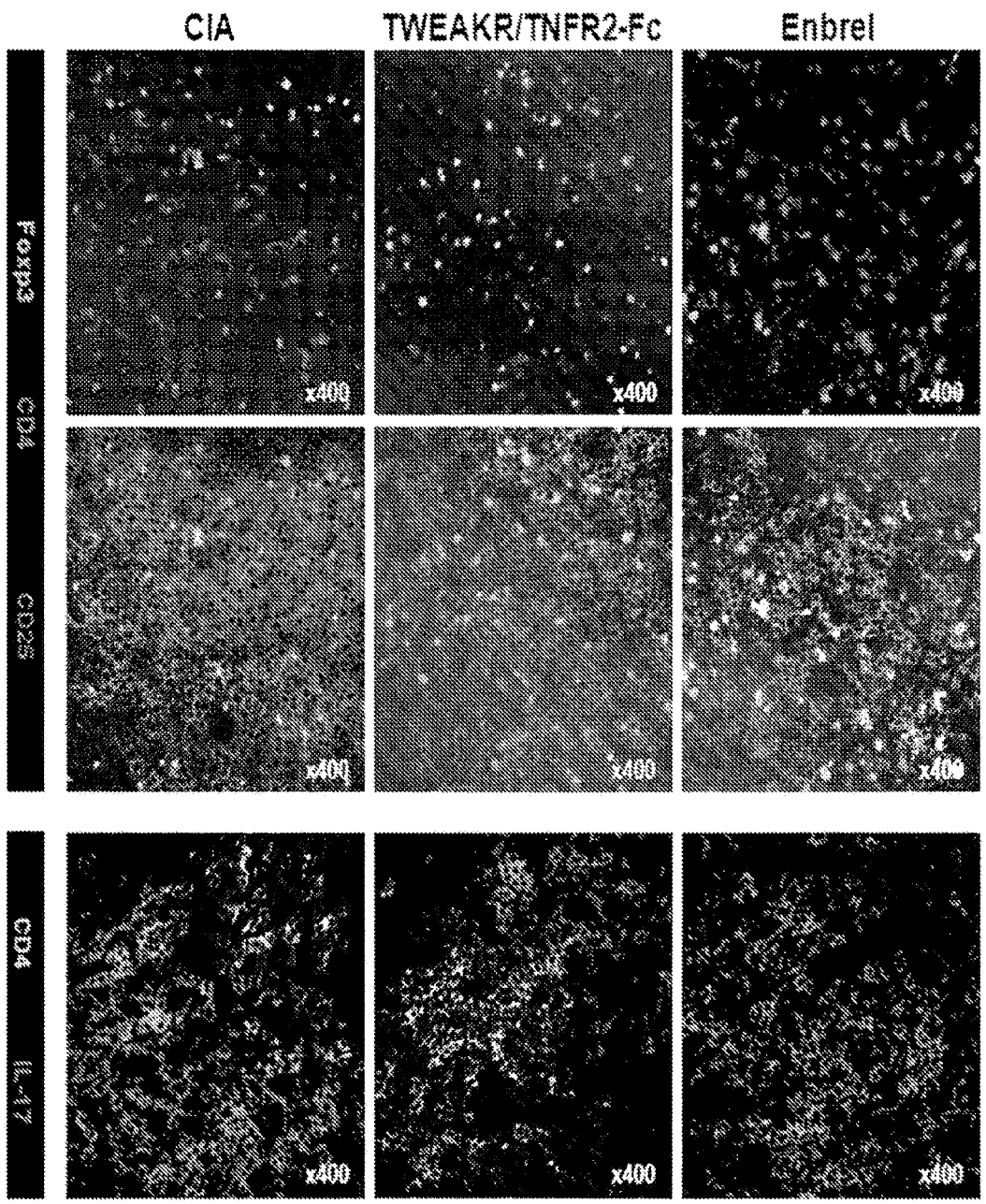

FIG. 19 is a set of photographs illustrating the expressions of Th17 and Treg cells in the spleen of CIA mouse model, confirmed by immunostaining method:
CIA: negative control—CIA (collagen induced arthritis) animal model group treated with nothing;
TNFR2-TWEAKR-Fc: CIA animal model group treated with TNFR2-TWEAKR fusion protein; and
Enbrel: CIA animal model group treated with the arthritis treatment agent Enbrel.

DESCRIPTION OF THE PREFERRED EMBODIMENTS

Hereinafter, the present invention is described in detail.
The present invention provides a fusion protein in which the fragment containing TNFR2 (tumor necrosis factor receptor type 2) protein or extracellular domain of the said TNFR2 is linked to the fragment containing TWEAKR (TNF-related weak inducer of apoptosis receptor) protein or extracellular domain of the said TWEAKR.

In the TNFR2-TWEAKR fusion protein, the fragment containing extracellular domain of TNFR2 is preferably the polypeptide containing the sequence ranging from the $23^{rd}$ ~$179^{th}$ residue of the amino acid sequence represented by SEQ. ID. NO: 2, but not always limited thereto. In the TNFR2-TWEAKR fusion protein, the fragment containing extracellular domain of TWEAKR is preferably the polypeptide containing the sequence ranging from the $28^{th}$~$76^{th}$ residue of the amino acid sequence represented by SEQ. ID. NO: 3, but not always limited thereto. The TNFR2-TWEAKR fusion protein preferably has the amino acid sequence represented by SEQ. ID. NO: 1, but not always limited thereto. It is also preferred that the TNFR2-TWEAKR fusion protein is composed of 200~250 amino acids, but not always limited thereto.

The TNFR2-TWEAKR fusion protein preferably contains the fragment originated from constant domain of antibody heavy chain, but not always limited thereto. Fc domain included in the TNFR2-TWEAKR fusion protein is preferably selected from the group consisting of IgA, IgD, IgE, IgG, and IgM, and more preferably it contains the whole or a part of CH2 and CH3 constant domain, but not always limited thereto. In the TNFR2-TWEAKR fusion protein, carboxyl-terminal and amino-terminal of extracellular soluble domains of TNFR2 and TWEAKR preferably contain the whole or a part of constant domain of antibody heavy chain, but not always limited thereto.

The TNFR2-TWEAKR fusion protein of the present invention is preferably prepared by the method comprising the following steps, but not always limited thereto:

1) performing PCR (polymerase chain reaction) with TWEAKR primer using DNA library as a template;
2) performing PCR with TNFR2 primer using DNA library as a template;
3) performing PCR with a primer encoding TNFR2-TWEAKR fusion gene using the PCR products of step 1) and step 2) as templates;
4) digesting the PCR product of step 3) with a restriction enzyme;
5) digesting the expression vector pYK-602-HIS-Fc with a restriction enzyme;
6) performing ligation of the plasmids digested with the restriction enzymes of step 4) and step 5);
7) transforming the TNFR2-TWEAKR fusion protein completed with the ligation reaction of step 6);
8) inoculating the protein on LB plate after completion of the transformation of step 7);
9) performing PCR using the colony generated in step 8);
10) transfecting 293E cells with the TNFR2-TWEAKR fusion protein confirmed in step 9);
11) purifying the TNFR2-TWEAKR fusion protein expressed in the 293E cells of step 10) from the cell culture medium;
12) eliminating cytotoxicity from the TNFR2-TWEAKR fusion protein purified in step 11); and
13) confirming binding affinity of the TNFR2-TWEAKR fusion protein purified in step 12).

In the preparation method of the present invention, the construction of the vector is preferably performed by PCR using DNA library, and the said DNA library is preferably constructed from liver, placenta, pancreas, and liver tissues, but not always limited thereto.

The present invention also provides a polynucleotide encoding the TNFR2-TWEAKR fusion protein.

The present invention further provides an expression vector containing the polynucleotide encoding the TNFR2-TWEAKR fusion protein.

The expression vector containing the polynucleotide encoding the TNFR2-TWEAKR fusion protein is preferably pYK602-HIS-Fc, but not always limited thereto.

The present invention also provides a transformant obtained by transfecting host cells with the expression vector containing the polynucleotide encoding the TNFR2-TWEAKR fusion protein.

In the TNFR2-TWEAKR fusion protein, the fragment containing extracellular domain of TNFR2 is preferably the polypeptide containing the sequence ranging from the $23^{rd}$ ~$179^{th}$ residue of the amino acid sequence represented by SEQ. ID. NO: 2, but not always limited thereto. In the TNFR2-TWEAKR fusion protein, the fragment containing extracellular domain of TWEAKR is preferably the polypeptide containing the sequence ranging from the $28^{th}$~$76^{th}$ residue of the amino acid sequence represented by SEQ. ID. NO: 3, but not always limited thereto. The TNFR2-TWEAKR fusion protein preferably has the amino acid sequence represented by SEQ. ID. NO: 1, but not always limited thereto. It is also preferred that the TNFR2-TWEAKR fusion protein is composed of 200~250 amino acids, but not always limited thereto.

The TNFR2-TWEAKR fusion protein preferably contains the fragment originated from constant domain of antibody heavy chain, but not always limited thereto. Fc domain included in the TNFR2-TWEAKR fusion protein is preferably selected from the group consisting of IgA, IgD, IgE, IgG, and IgM, and more preferably it contains the whole or a part of CH2 and CH3 constant domain, but not always limited thereto. In the TNFR2-TWEAKR fusion protein, carboxyl-terminal and amino-terminal of extracellular soluble domains of TNFR2 and TWEAKR preferably contain the whole or a part of constant domain of antibody heavy chain, but not always limited thereto.

The transformant containing the polynucleotide encoding the TNFR2-TWEAKR fusion protein is preferably E. coli DH5α, but not always limited thereto.

In a preferred embodiment of the present invention, TWEAKR and TNFR2 genes were amplified by PCR to subclone TWEAKR and TNFR2 into the expression vector pYK602-HIS-Fc. Each of the amplified PCR products was ligated in the expression vector pYK602-HIS-Fc to construct TNFR2-Fc and TWEAKR-Fc (see FIG. 1 and FIG. 3). The constructed TNFR2-Fc and TWEAKR-Fc were transfected in 293E cells. Upon completion of the transfection, the produced and purified protein was confirmed (see FIG. 2 and FIG. 4).

TWEAKR and TNFR2 genes were amplified by PCR using DNA library mixture as a template. After constructing a primer to amplify TWEAKR and TNFR2 fusion gene (see FIG. 5), PCR was performed with the gene encoding TNFR2-TWEAKR fusion protein by using the amplified product above as a template. The polypeptide encoding TNFR2-TWEAKR fusion protein was amplified by PCR. The amplified PCR product proceeded to ligation into the expression vector pYK602-HIS-Fc, leading to the construction of TNFR2-TWEAKR fusion protein (see FIG. 6). The constructed TNFR2-TWEAKR fusion protein was transfected into 293E cells, and the protein produced thereby was purified and identified (see FIG. 7 and FIG. 8).

For the mass-production of TNFR2-Fc, TWEAKR-Fc, and TNFR2-TWEAKR fusion protein, 293E cells were transfected with TNFR2-Fc, TWEAKR-Fc, and TNFR2-TWEAKR fusion protein considering the expression rate, and the fusion proteins produced thereby were purified and identified (see Table 1, Table 2 and FIG. 9).

Cytotoxicity of the prepared TNFR2-Fc, TWEAKR-Fc, and TNFR2-TWEAKR fusion protein was investigated, and if there were any, it would be eliminated (see Table 3, Table 4).

In addition, binding affinity between TNFR2-Fc, TWEAKR-Fc, and TNFR2-TWEAKR fusion protein and their ligand TNF-α or TWEAK was investigated. As a result, TNFR2-Fc demonstrated high binding affinity to TNF-α, and TWEAKR-Fc also demonstrated high binding affinity to TWEAK. In the meantime, TNFR2-TWEAKR fusion protein demonstrated high binding affinity to both TNF-α and TWEAK (see FIG. 10).

The present invention also provides a composition for the prevention and treatment of autoimmune disease comprising the TNFR2-TWEAKR fusion protein as an active ingredient.

In the TNFR2-TWEAKR fusion protein, the fragment containing extracellular domain of TNFR2 is preferably the polypeptide containing the sequence ranging from the $23^{rd}$ ~$179^{th}$ residue of the amino acid sequence represented by SEQ. ID. NO: 2, but not always limited thereto. In the TNFR2-TWEAKR fusion protein, the fragment containing extracellular domain of TWEAKR is preferably the polypeptide containing the sequence ranging from the $28^{th}$~$76^{th}$ residue of the amino acid sequence represented by SEQ. ID. NO: 3, but not always limited thereto. The TNFR2-TWEAKR fusion protein preferably has the amino acid sequence represented by SEQ. ID. NO: 1, but not always limited thereto. It is also preferred that the TNFR2-TWEAKR fusion protein is composed of 200~250 amino acids, but not always limited thereto.

The TNFR2-TWEAKR fusion protein preferably contains the fragment originated from constant domain of antibody heavy chain, but not always limited thereto. Fc domain included in the TNFR2-TWEAKR fusion protein is preferably selected from the group consisting of IgA, IgD, IgE, IgG, and IgM, and more preferably it contains the whole or a part of CH2 and CH3 constant domain, but not always limited thereto. In the TNFR2-TWEAKR fusion protein, carboxyl-terminal and amino-terminal of extracellular soluble domains of TNFR2 and TWEAKR preferably contain the whole or a part of constant domain of antibody heavy chain, but not always limited thereto.

The said autoimmune disease is preferably the one selected from the group consisting of autoimmune rheumatoid arthritis, lupus, myasthenia gravis, ankylosing spondylitis, hyperthyroidism, hypothyroidism, ulcerative colitis, Crohn's disease, valvular heart disease, multiple sclerosis, Scleroderma, and autoimmune hepatitis, and more preferably autoimmune rheumatoid arthritis, but not always limited thereto.

In a preferred embodiment of the present invention, the expressions of TWEAK, TWEAKR, IL-17, and receptor activator of nuclear factor kappa B ligand (RANKL) in synovial membrane tissues of autoimmune arthritis patient and Osteoarthritis (OA) patient were investigated and compared. As a result, in the case of autoimmune arthritis patient, the expressions of TWEAK, TWEAKR, IL-17, and RANKL were higher than those shown in OA patient (see FIG. 11). Th17 cells were treated with TNFR2-Fc, TWEAKR-Fc, and TNFR2-TWEAKR fusion protein constructed in an example of the invention, followed by the investigation of the expressions of IL-21, IL-17, and RORc. As a result, all the expressions of IL-21, IL-17, and RORc were significantly decreased (see FIG. 12). Th17 cells were treated with TNFR2-Fc, TWEAKR-Fc, and TNFR2-TWEAKR fusion protein, then, the expression of the inflammatory cytokine IL-17 secreted in Th17 cells was measured by ELISA. As a result, the secretion of IL-17 was significantly reduced when TNFR2-TWEAKR fusion protein was treated, compares with when TNFR2-Fc or TWEAKR-Fc was treated (see FIG. 12). After treating TNFR2-Fc, TWEAKR-Fc, and TNFR2-TWEAKR fusion protein, the secretion of the anti-inflammatory cytokine IL-10 was measured by ELISA. As a result, the secretion of IL-10 was increased when TNFR2-TWEAKR fusion protein was treated compared with when TNFR2-Fc and TWEAKR-Fc were treated, (see FIG. 13). In addition, the levels of TWEAK and RANKL in serum and synovial fluid of autoimmune arthritis patients and OA patients were measured by ELISA. As a result, both of TWEAK and RANKL were significantly increased in serum and synovial fluid with interacting each other (see FIG. 14).

In a preferred embodiment of the present invention, CIA (collagen induced arthritis) mouse model was constructed to confirm the in vivo treatment effect of the TNFR2-TWEAKR fusion protein of the present invention on arthritis. Then, the mouse model was treated with the TNFR2-TWEAKR fusion protein of the present invention. As a result, the treatment effect on arthritis was confirmed (see FIG. 15). Precisely, infiltration and inflammation in joint was reduced and so was cartilage destruction (see FIG. 16). The expressions of inflammatory factors were also reduced (see FIG. 17), and the generation of CII specific IgG2a, administered to construct the arthritis induced mouse model, was inhibited (see FIG. 18). The arthritis treatment effect or alleviation effect of the fusion protein of the present invention was similar to or better than that of Enbrel, being used as of today as an arthritis treatment agent. Spleen tissue involved in immune response was extracted from the CIA mouse model treated with the TNFR2-TWEAKR fusion protein of the present invention, followed by observation of the expressions of Th17 and Treg cells. As a result, the expression of Th17 cells (CD4+IL-17+) expressing inflammatory factors was decreased, while the expression of Treg cells (CD4+CD25+Foxp3+), the immune suppressive cells, protecting cells from autoimmune response was increased (see FIG. 19).

In conclusion, the TNFR2-TWEAKR fusion protein of the present invention reduces the inflammatory cytokine IL-17 production, which is more significant than TNFR2-Fc and TWEAKR-Fc do, increases the anti-inflammatory cytokine IL-generation better than TNFR2-Fc and TWEAKR-Fc do, and demonstrates autoimmune rheumatoid arthritis alleviation or treatment effect in CIA mouse model. Therefore, the TNFR2-TWEAKR fusion protein of the present invention can be effectively used as an active ingredient for the composition for the prevention and treatment of autoimmune disease.

The pharmaceutically effective dosage of the TNFR2-TWEAKR fusion protein of the present invention can be determined by considering various factors such as administration method, target area, patient condition, etc. Thus, the dosage for human body has to be determined with the consideration of safety and efficiency at the same time. It is also possible to predict the effective dosage based on the effective dosage confirmed by animal test. Various factors that have to be considered for the determination of the effective dosage are described in the following articles: Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The pharmaceutical composition of the present invention can include any generally used carrier, diluent, excipient, or a combination of at least two of those. The pharmaceutically acceptable carrier can be any carrier that is able to deliver the TNFR2-TWEAKR fusion protein of the present invention in human body without limitation, which is exemplified by the compounds described in Merck Index, 13$^{th}$ ed., Merck & Co. Inc., such as saline, sterilized water, Ringer's solution, buffered saline, dextrose solution, maltodextrin solution, glycerol, ethanol, liposome and a mixture comprising one or more of those components. If necessary, a general additive such as antioxidant, buffer, and bacteriostatic agent can be additionally added. The composition of the present invention can be formulated in different forms including aqueous solutions, suspensions and emulsions for injection, pills, capsules, granules or tablets by mixing with diluents, dispersing agents, surfactants, binders and lubricants. The composition can further be prepared in suitable forms according to ingredients by following the method represented in Remington's Pharmaceutical Science Mack Publishing Company, Easton Pa., 18th, 1990).

The composition of the present invention can additionally include one or more effective ingredients having the same or similar function to the active ingredient. The composition of the present invention can include the said protein by 0.0001~10 weight %, and preferably by 0.001~1 weight % by the total weight of the composition.

The pharmaceutical composition of the present invention can be administered orally or parenterally (for example, intravenous, hypodermic, peritoneal or local injection). The effective dosage of the composition can be determined according to weight, age, gender, health condition, diet, administration frequency, administration method, excretion and severity of a disease. The dosage is 0.001 μg ~10 mg/kg per day and preferably 0.01 μg ~10 mg/kg per day, and administration frequency is once a day or preferably a few times a day.

The present invention also provides a method for the treatment of autoimmune disease containing the step of administering pharmaceutically effective dose of the TNFR2-TWEAKR fusion protein to a subject having autoimmune disease.

The present invention also provides a method for the prevention of autoimmune disease containing the step of administering pharmaceutically effective dose of the TNFR2-TWEAKR fusion protein to a subject.

In the TNFR2-TWEAKR fusion protein, the fragment containing extracellular domain of TNFR2 is preferably the polypeptide containing the sequence ranging from the 23$^{rd}$~179$^{th}$ residue of the amino acid sequence represented by SEQ. ID. NO: 2, but not always limited thereto. In the TNFR2-TWEAKR fusion protein, the fragment containing extracellular domain of TWEAKR is preferably the polypeptide containing the sequence ranging from the 28$^{th}$~76$^{th}$ residue of the amino acid sequence represented by SEQ. ID. NO: 3, but not always limited thereto. The TNFR2-TWEAKR fusion protein preferably has the amino acid sequence represented by SEQ. ID. NO: 1, but not always limited thereto. It is also preferred that the TNFR2-TWEAKR fusion protein is composed of 200~250 amino acids, but not always limited thereto.

The TNFR2-TWEAKR fusion protein preferably contains the fragment originated from constant domain of antibody heavy chain, but not always limited thereto. Fc domain included in the TNFR2-TWEAKR fusion protein is preferably selected from the group consisting of IgA, IgD, IgE, IgG, and IgM, and more preferably it contains the whole or a part of CH2 and CH3 constant domain, but not always limited thereto. In the TNFR2-TWEAKR fusion protein, carboxyl-terminal and amino-terminal of extracellular soluble domains of TNFR2 and TWEAKR preferably contain the whole or a part of constant domain of antibody heavy chain, but not always limited thereto.

The said autoimmune disease is preferably the one selected from the group consisting of autoimmune rheumatoid arthritis, lupus, myasthenia gravis, ankylosing spondylitis, hyperthyroidism, hypothyroidism, ulcerative colitis, Crohn's disease, valvular heart disease, multiple sclerosis, Scleroderma, and autoimmune hepatitis, and more preferably autoimmune rheumatoid arthritis, but not always limited thereto.

It was confirmed that the TNFR2-TWEAKR fusion protein of the present invention reduced the production of the inflammatory cytokine IL-17, which was more significant than TNFR2-Fc and TWEAKR-Fc did, but increased the production of the anti-inflammatory cytokine IL-10 better than TNFR2-Fc and TWEAKR-Fc did. Therefore, the TNFR2-TWEAKR fusion protein can be effectively used for the treatment of autoimmune disease by administering pharmaceutically effective dose of the TNFR2-TWEAKR fusion protein to a subject having autoimmune disease.

The pharmaceutically effective dosage of the TNFR2-TWEAKR fusion protein of the present invention can be determined by considering various factors such as administration method, target area, patient condition, etc. Thus, the dosage for human body has to be determined with the consideration of safety and efficiency at the same time. It is also possible to predict the effective dosage based on the effective dosage confirmed by animal test. Various factors that have to be considered for the determination of the effective dosage are described in the following articles: Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The pharmaceutical composition of the present invention can include any generally used carrier, diluent, excipient, or a combination of at least two of those. The pharmaceutically acceptable carrier can be any carrier that is able to deliver the TNFR2-TWEAKR fusion protein of the present invention in human body without limitation, which is exemplified by the compounds described in Merck Index, 13$^{th}$ ed., Merck & Co. Inc., such as saline, sterilized water, Ringer's solution, buffered saline, dextrose solution, maltodextrin solution, glycerol, ethanol, liposome and a mixture comprising one or more of those components. If necessary, a general additive such as antioxidant, buffer, and bacteriostatic agent can be additionally added. The composition of the present invention can be formulated in different forms including aqueous solutions, suspensions and emulsions for injection, pills, capsules, granules or tablets by mixing with diluents, dispersing agents, surfactants, binders and lubricants. The composition can further be prepared in suitable forms according to ingredients by following the method represented in Remington's Pharmaceutical Science Mack Publishing Company, Easton Pa., 18th, 1990).

The composition of the present invention can additionally include one or more effective ingredients having the same or similar function to the active ingredient. The composition of the present invention can include the said protein by 0.0001~10 weight %, and preferably by 0.001~1 weight % by the total weight of the composition.

The pharmaceutical composition of the present invention can be administered orally or parenterally (for example, intravenous, hypodermic, peritoneal or local injection). The effective dosage of the composition can be determined according to weight, age, gender, health condition, diet, administration frequency, administration method, excretion and severity of a disease. The dosage is 0.001 μg ~10 mg/kg per day and preferably 0.01 μg ~10 mg/kg per day, and administration frequency is once a day or preferably a few times a day.

In addition, the present invention provides TNFR2-TWEAKR fusion protein for the prevention and treatment of autoimmune disease.

In the TNFR2-TWEAKR fusion protein, the fragment containing extracellular domain of TNFR2 is preferably the polypeptide containing the sequence ranging from the $23^{rd}$~$179^{th}$ residue of the amino acid sequence represented by SEQ. ID. NO: 2, but not always limited thereto. In the TNFR2-TWEAKR fusion protein, the fragment containing extracellular domain of TWEAKR is preferably the polypeptide containing the sequence ranging from the $28^{th}$~$76^{th}$ residue of the amino acid sequence represented by SEQ. ID. NO: 3, but not always limited thereto. The TNFR2-TWEAKR fusion protein preferably has the amino acid sequence represented by SEQ. ID. NO: 1, but not always limited thereto. It is also preferred that the TNFR2-TWEAKR fusion protein is composed of 200~250 amino acids, but not always limited thereto.

The TNFR2-TWEAKR fusion protein preferably contains the fragment originated from constant domain of antibody heavy chain, but not always limited thereto. Fc domain included in the TNFR2-TWEAKR fusion protein is preferably selected from the group consisting of IgA, IgD, IgE, IgG, and IgM, and more preferably it contains the whole or a part of CH2 and CH3 constant domain, but not always limited thereto. In the TNFR2-TWEAKR fusion protein, carboxyl-terminal and amino-terminal of extracellular soluble domains of TNFR2 and TWEAKR preferably contain the whole or a part of constant domain of antibody heavy chain, but not always limited thereto.

The said autoimmune disease is preferably the one selected from the group consisting of autoimmune rheumatoid arthritis, lupus, myasthenia gravis, ankylosing spondylitis, hyperthyroidism, hypothyroidism, ulcerative colitis, Crohn's disease, valvular heart disease, multiple sclerosis, Scleroderma, and autoimmune hepatitis, and more preferably autoimmune rheumatoid arthritis, but not always limited thereto.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

EXAMPLE 1

Construction of TWEAKR-Fc

<1-1> Construction of TWEAKR-Fc Expression Vector

To construct TWEAKR-Fc expression vector, TWEAKR gene was amplified by PCR using DNA library mixture (mixture of kidney, placenta, pancreas, and liver; purchased from 21C Frontier Human GENE Bank (Korea Research Institute of Bioscience and Biotechnology), Clone ID: Ku012783, plate No. UG-0134-G10, vector: pCNS) as a template with F228 forward primer containing SfiI site (SEQ. ID. NO: 4: 5'-CAGGGGGCCGTGGGGGCCGAGCAAGCGC-CAGGCACCGC-3'), F228 reverse primer (SEQ. ID. NO: δ: 5'-TAGCGGCCGACGCGGCCAAT-TCAGCTGGGGGGCTGGGGC-3'), F448 forward primer (SEQ. ID. NO: δ: 5'-CAGGGGGCCGTGGGGGC-CAGTTTGGGGAGCCGGGCATC-3'), and F448 reverse primer (SEQ. ID. NO: 7: 5'-TAGCGGCCGACGCGGC-CAAGTGAACCTGGAAGAGTCCGA-3'). The PCR product was treated with SfiI, and then subcloned into pYK602-HIS-Fc. PCR reaction mixture was prepared as follows. 100 ng of template DNA, 2.5 unit of pfu polymerase (Genotech, Korea), 10 pmole/50 μl of each primer, and distilled water were mixed to make the final volume 50 μl. PCR was performed as follows; predenaturation at 94° C. for 2 minutes, denaturation at 94° C. for 30 seconds, annealing at 55° C. for 30 seconds, polymerization at 72° C. for 30 seconds, 30 cycles from denaturation to polymerization, and final extension at 72° C. for 10 minutes.

The amplified PCR product and the vector were digested with SfiI, followed by reaction at 37° C. for 4 hours. Purification was then performed by using gel purification kit (QIAGEN, #28706, USA). The ratio of the amplified PCR product to the vector was 3(150 μg):1(50 μg), to which 1 μl of T4 DNA ligase (#SDL01-R40k, Solgent, Korea) and 2 μl of 10× ligase buffer were added to make total volume of the reaction solution 20 μl, followed by ligation at 16° C. for 16 hours.

*E. coli* DH5α was transformed with the ligated plasmid, which was spread on LB plate containing ampicillin, followed by incubation in a 37° C. incubator for 16 hours. The generated colony was resuspended in LB medium containing 10 μl of ampicillin, followed by colony PCR using 4~5 μl of the medium as a template. As a result, it was confirmed that TWEAKR gene was successfully subcloned in the expression vector.

<1-2> Expression and Purification of TWEAKR-Fc 293E cells were cultured in 500 ml of DMEM supplemented with 50 ml of FBS, which was seeded in 150 mm plate (#430599, Corning, USA) with 70~80% confluency. TWEAKR-Fc expression vector was mixed with PEI (polyethylenimine, #23966, Polysciences, USA) at the ratio of 1:2 (20 μg: 40 μg), followed by reaction at room temperature for 20 minutes, which was dropped onto the cells for transfection. 16~20 hours later, the medium was replaced with 20 ml of serum-free DMEM and the supernatant was obtained every 2~3 days. The obtained supernatant was centrifuged at 5000 rpm for 10 minutes. The resultant supernatant was transferred in a new bottle, which was stored at 4° C. until purification.

Total 600 ml of the supernatant was obtained from 10 150 mm plates on day 3, day 5, and day 7, which proceeded to purification. The total supernatant was filtered with 0.22 μm top-filter (#PR02890 Millipore USA), which was then bound to 500 μl of protein A beads (#17-1279-03, GE healthcare, Sweden) packed in 5 ml column. Binding reaction was induced at 4° C. for overnight by using Peri-start pump (0.9 ml/minute). The column was washed with at least 100 ml of PBS. Elution was performed by using 0.1 M GLycine-HCl (#G7126, Sigma, USA) to give 6 fractions, followed by neutralization with 1 M Tris (#T-1503-5KG, Sigma, USA) (pH 9.0). Then, TWEAKR-Fc was quantified. 2~3 fractions showing TWEAKR-Fc expression were collected and concentrated by using amicon ultra (#UFC805024, Millipore, USA). Buffer was replaced with fresh PBS (#70011, Gibco, USA) about 10 times.

Figure 1:
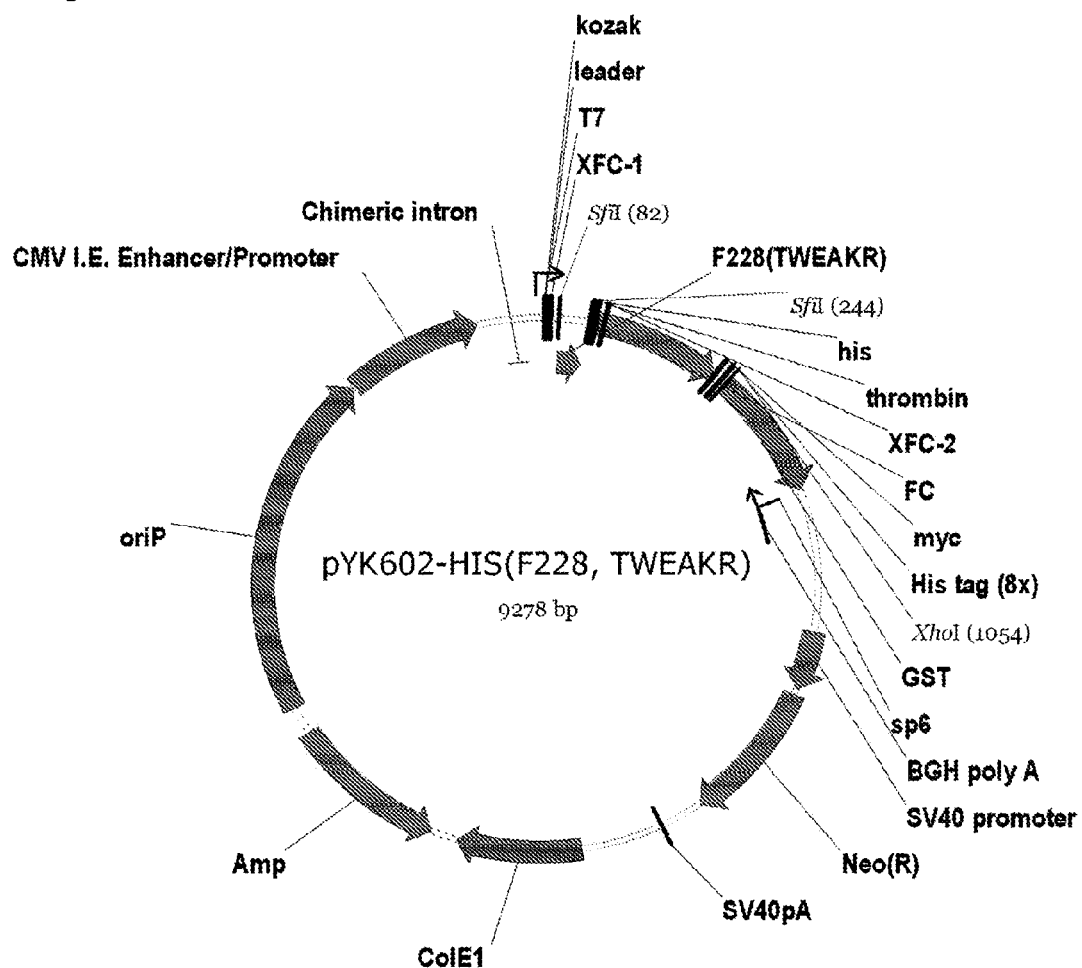
FIG. 1 is a diagram illustrating the structure of TWEAKR-Fc in which TWEAKR gene has been cloned in the expression vector pYK602-HIS-Fc.
Figure 2:
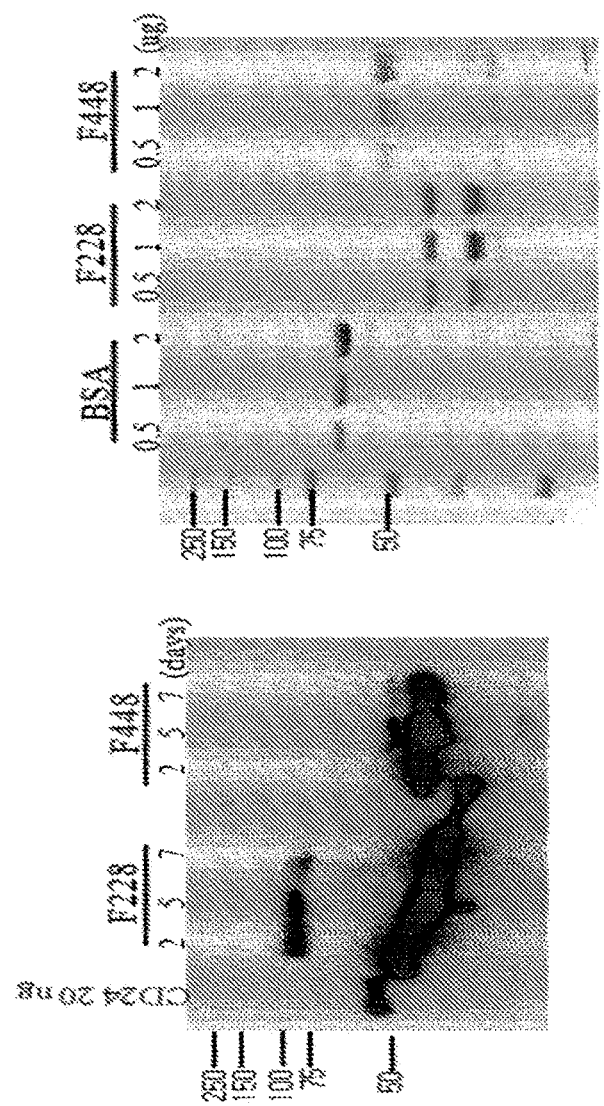
FIG. 2 is a set of photographs illustrating the result of western blot confirming the expression of TWEAKR-Fc cloned in the expression vector pYK602-HIS-Fc, and the result of another western blot using HIS antibody performed after purifying the expressed protein by using protein A beads.

As a result, as shown in FIG. 2, total 1.9 mg of TWEAKR-Fc was obtained (960 μg/μg) (FIG. 1 and FIG. 2).

EXAMPLE 2

Construction of TNFR2-Fc

<2-1> Construction of TNFR2-Fc Expression Vector

To construct TNFR2-Fc expression vector, TNFR2 gene was amplified by PCR using DNA library mixture (mixture of kidney, placenta, pancreas, and liver; purchased from 21C Frontier Human GENE Bank (Korea Research Institute of Bioscience and Biotechnology), Clone ID: hMU013725, plate No. IRAU-86-H09, vector: pDNR-LIB) as a template with a forward primer containing SfiI site (SEQ. ID. NO: 8: 5'-CAGGGGGCCGTGGGGGCCTTGCCCGC-CCAGGTGGCATT-3') and a reverse primer (SEQ. ID. NO: 9: 5'-TAGCGGCCGACGCGGCCAAT-TCAGCTGGGGGGCTGGGGC-3'). The PCR product was treated with SfiI, and then subcloned into pYK602-HIS-Fc. PCR reaction mixture was prepared as follows. 100 ng of template DNA, 2.5 unit of pfu polymerase (Genotech, Korea), 10 pmole/50 µl of each primer, and distilled water were mixed to make the final volume 50 µl. PCR was performed as follows; predenaturation at 94° C. for 2 minutes, denaturation at 94° C. for 30 seconds, annealing at 55° C. for 30 seconds, polymerization at 72° C. for 1 minute, 30 cycles from denaturation to polymerization, and final extension at 72° C. for 10 minutes.

The amplified PCR product and the vector were digested with SfiI, followed by reaction at 37° C. for 4 hours. Purification was then performed by using gel purification kit. The ratio of the amplified PCR product to the vector was 3(150 µg):1(50 µg), to which 1 µl of T4 DNA ligase and 2 µl of 10× ligase buffer were added to make total volume of the reaction solution 20 µl, followed by ligation at 16° C. for 16 hours.

E. coli DH5α was transformed with the ligated plasmid, which was spread on LB plate containing ampicillin, followed by incubation in a 37° C. incubator for 16 hours. The generated colony was resuspended in LB medium containing 10 µl of ampicillin, followed by colony PCR using 4~5 µl of the medium as a template. As a result, it was confirmed that TNFR2 gene was successfully subcloned in the expression vector pYK602-HIS-Fc (FIG. 3 and FIG. 4).

<2-2> Expression and purification of TNFR2-Fc 293E cells were cultured in 500 ml of DMEM supplemented with 50 ml of FBS, which was seeded in 150 mm plate with 70~80% confluency. TNFR2-Fc expression vector (20 µg) was mixed with PEI (40 µg) at the ratio of 1:2, followed by reaction at room temperature for 20 minutes, which was dropped onto the cells for transfection. 16~20 hours later, the medium was replaced with 20 ml of serum free DMEM and the supernatant was obtained every 2~3 days. The obtained supernatant was centrifuged at 5000 rpm for 10 minutes. The resultant supernatant was transferred in a new bottle, which was stored at 4° C. until purification.

Total 600 ml of the supernatant was obtained from 10 150 mm plates on day 3, day 5, and day 7, which proceeded to purification. The total supernatant was filtered with 0.22 µm top-filter, which was then bound to 500 µl of protein A beads packed in 5 ml column. Binding reaction was induced at 4° C. for overnight by using Peri-start pump (0.9 ml/minute). The column was washed with at least 100 ml of PBS. Elution was performed by using 0.1 M GLycine-HCl to give 6 fractions, followed by neutralization with 1 M Tris (pH 9.0). Then, the purified TNFR2-Fc was quantified. 2~3 fractions showing TNFR2-Fc expression were collected and concentrated by using amicon ultra. Buffer was replaced with fresh PBS (#70011, Gibco, USA) about 10 times.

As a result, as shown in FIG. 4, total 235 µg of TNFR2-Fc was obtained (300 µg/ml).

EXAMPLE 3

Preparation of TNFR2-TWEAKR Fusion Protein

<3-1> Construction of TNFR2-TWEAKR Fusion Protein Expression Vector

To construct the expression vector for TNFR2-TWEAKR fusion protein, TNFR2 gene was amplified by PCR using DNA library mixture (mixture of kidney, placenta, pancreas, and liver) as a template with a forward primer containing SfiI site and a reverse primer (SEQ. ID. NO: 10: 5'-GCGGTGC-CTGGCGCTTGCTCCGTGCAGACTGCATCCATGCT-3'). TWEAKR gene was also amplified by PCR with a forward primer (SEQ. ID. NO: 11: 5'-AGCATGGATGCAGTCTGCACGGAG-CAAGCGCCAGGCACCGC-3') and a reverse primer under the following conditions. Two PCR products were mixed at the ratio of 1:1, which became a template at the volume of 100 ng, which proceeded to PCR with three primers, leading to subcloning of TNFR2-TWEAKR fusion protein into pYK602-HIS-Fc vector. PCR reaction mixture was prepared as follows. 100 ng of template DNA, 2.5 unit of pfu polymerase (Genotech, Korea), 10 pmole/50 µl of each primer, and distilled water were mixed to make the final volume 50 µl. PCR was performed as follows; predenaturation at 94° C. for 2 minutes, denaturation at 94° C. for 30 seconds, annealing at 55° C. for 30 seconds, polymerization at 72° C. for 1 minute, 30 cycles from denaturation to polymerization, and final extension at 72° C. for 10 minutes.

Each of the amplified PCR products was digested with SfiI, followed by reaction at 37° C. for 4 hours. Purification was then performed by using gel purification kit. The PCR product and the vector were mixed at the ratio of 3 (150 µg):1(50 µg), to which 1 µl of T4 DNA ligase and 2 µl of 10× ligase buffer were added to make total volume of the reaction solution 20 µl, followed by ligation at 16r for 16 hours.

E. coli DH5α was transformed with the ligated plasmid, which was spread on LB plate containing ampicillin, followed by incubation in a 37° C. incubator for 16 hours. The generated colony was resuspended in LB medium containing 10 µl of ampicillin, followed by colony PCR using 4~5 µl of the medium as a template. As a result, it was confirmed that the polynucleotide encoding TNFR2-TWEAKR fusion protein was successfully subcloned in the expression vector pYK602-HIS-Fc.

<3-2> Expression and Purification of TNFR2-TWEAKR Fusion Protein 293E cells were cultured in 500 ml of DMEM supplemented with 50 ml of FBS, which was seeded in 150 mm plate with 70~80% confluency. TNFR2-TWEAKR fusion protein (20 µg) was mixed with PEI (40 µg) at the ratio of 1:2, followed by reaction at room temperature for 20 minutes, which was dropped onto the cells for transfection. 16~20 hours later, the medium was replaced with 20 ml of serum free DMEM and the supernatant was obtained every 2~3 days. The obtained supernatant was centrifuged at 5000 rpm for 10 minutes. The resultant supernatant was transferred in a new bottle, which was stored at 4° C. until purification.

Total 600 ml of the supernatant was obtained from 10 150 mm plates on day 3, day 5, and day 7, which proceeded to purification. The total supernatant was filtered with 0.22 µm top-filter, which was then bound to 500 µl of protein A beads packed in 5 ml column. Binding reaction was induced at 4° C. for overnight by using Peri-start pump (0.9 ml/minute). The column was washed with at least 100 ml of PBS. Elution was performed by using 0.1 M GLycine-HCl to give 6 fractions, followed by neutralization with 1 M Tris (pH 9.0). Then, the purified TNFR2-TWEAKR fusion protein was quantified. 2~3 fractions showing TNFR2-TWEAKR fusion protein expression were collected and concentrated by using amicon ultra. Buffer was replaced with fresh PBS (#70011, Gibco, USA) about 10 times.

As a result, as shown in FIG. 7, total 1 mg of TNFR2-TWEAKR fusion protein was obtained (380 µg/ml).

EXAMPLE 4

Mass-purification of TNFR2-TWEAKR Fusion Protein

<4-1> Transfection

When 293E cells cultured on 150 mm plate (#430599, Corning, USA) were grown to 80%~90% confluency, transfection was performed. The ratio of PEI to TNFR2-TWEAKR fusion protein was 2:1, that is 20 µg of plasmid DNA was mixed with 40 µg of PEI on 150 mm plate. The PEI/plasmid DNA mixed solution was added to 1 ml of serum-free medium, followed by mixing with Vortex. After 20 minute-reaction at room temperature, 1 ml of the reaction solution was distributed on 150 mm plate. To increase transfection efficiency, reaction was induced at 37° C. in a $CO_2$ incubator for 24 hours and then the 150 mm plate was washed with PBS to eliminate PEI and plasmid DNA. 20 ml of serum-free medium was distributed on 150 mm plate above, followed by incubation in a $CO_2$ incubator for 24 hours.

<4-2> Supernatant Sampling

Supernatant sampling was performed every other day 5 times and the total volume of the supernatant obtained from one 150 mm plate was about 100 ml. Taking the expression amount of each sample shown in Table 1 (expression vector, TNFR2-Fc, TWEAKR-Fc, and TNFR2-TWEAKR fusion protein) into consideration, the volume obtainable from mass-purification was predicted and the necessary amount of culture solution was calculated. The necessary volume of the culture solution to obtain 1 mg of each TNFR2-Fc, TWEAKR-Fc, TNFR2-TWEAKR fusion protein, and the control expression vector is shown in Table 2 (Table 1 and Table 2).

TABLE 1

| Sample | Expression Amount |
|---|---|
| Expression Vector | 1.0 mg/l |
| TNFR2-Fc | 0.6 mg/l |
| TWEAKR-Fc | 0.6 mg/l |
| TNFR2-TWEAKR fusion protein | 0.6 mg/l |

TABLE 2

| Sample | Expression Amount |
|---|---|
| Expression Vector | 1 l |
| TNFR2-Fc | 2 l |
| TWEAKR-Fc | 2 l |
| TNFR2-TWEAKR fusion protein | 2 l |

<4-3> Purification

Culture supernatant was filtered with 0.22 µm Top-filter, and the filtered supernatant was loaded in a sterilized 1 l bottle, followed by purification in a cold chamber. Purification was performed by using Peristart-pump. The purification column was washed with PBS by using an injector at the speed of 2 ml/min for 30 minutes. Then, protein A beads were packed in the column. When the volume of supernatant was 1 l, the volume of protein A beads used was approximately 700 µl. After packing protein A beads, the column was washed with 50 ml of PBS again. Then, culture supernatant was loaded in the column. At that time, the speed was set at 1 ml/min to induce binding for overnight. On the next day, the column was washed again with 200 ml of PBS at the speed of 2 ml/min, followed by elution. The concentration of the eluted protein was measured, and then buffer was replaced with PBS, which was stored at 4° C. Purification purity was confirmed by electrophoresis on 10% SDS-PAGE gel for QC test (FIGS. 7, 8, and 9).

EXPERIMENTAL EXAMPLE 1

Elimination of Cytotoxicity from the Purified Fusion Protein

<1-1> Toxicity Test

After purifying the fusion proteins (TNFR2-Fc, TWEAKR-Fc, and TNFR2-TWEAKR fusion protein) prepared in the above example, bacterial endotoxin in the purified protein was measured by using Crhomo-LAL (cat# C0031, CAPE COD). Control standard endotoxin (CSE; cat# E0005, CAPE COD), used as a control, was diluted starting from 1 EU/ml by two-folds to make the minimum concentration 0.03125 EU/ml. To prepare the negative control, 100 µl of LAL was added to 100 µl of LRW (LAL reagent water, cat# WP1001, CAPE COD). To prepare the positive control, 100 µl of LAL was added to 100 µlof CSE (0.125 EU/n1). 100 µl of LAL was added to 100 of the sample diluted with LRW at the concentration of 50 µg/g for further analysis. For the investigation of interference, 50 µl of CSE (0.125 EU/ml) and 100 µl of LAL were added to 50 µl of the diluted sample to prepare the product positive control. Standard value was determined by using the protocol-file (Chromo LAL setting. pda) made by the measurement with VersaMax microplate reader. The plate was pre-heated at 37° C. for 10 minutes. While treating LAL, the protocol-file ran at the same time, followed by measurement of OD. Standard curve was made with X-axis presenting Log EU/ml and Y-axis presenting Log Onset time. The value of cytotoxicity of the sample was calculated automatically by converting the value of OD with software, which was then presented by EU/ml. If $R^2$ value of standard curve was 0.98 or up, it was regarded that the measured value was reliable.

As a result, as shown in Table 3, 4 samples (expression vector, TNFR2-Fc, TWEAKR-Fc, and TNFR2-TWEAKR fusion protein) were confirmed to have cytotoxicity (Table 3).

TABLE 3

| Purified Sample | Cytotoxicity (EU/ml) |
|---|---|
| Expression Vector | 62.14 |
| TNFR2-Fc | 40.33 |
| TWEAKR-Fc | 171 |
| TNFR2-TWEAKR fusion protein | 171.52 |

<1-2> Elimination of Cytotoxicity

To eliminate cytotoxicity of the purified fusion protein, EndoTrap Red column (cat#83-009U, Lonza) was used. The column was washed with 3 ml of regeneration buffer twice, followed by another washing with equilibration buffer twice. At the moment of applying sample, fractions began to obtain simultaneously. At that time, flow rate of the sample was set at 0.5~1 ml/min. The sample left-over in the column was recovered by using 1 ml of equilibration buffer. After eliminating cytotoxicity, cytotoxicity test was performed by the same manner as described in Experimental Example <1-1> to confirm the elimination of cytotoxicity.

As a result, as shown in Table 4, the degree of cytotoxicity in the purified protein was reduced in every sample (Table 4).

TABLE 4

| Purified Sample | Cytotoxicity (EU/ml) |
| --- | --- |
| Expression Vector | 3.76 |
| TNFR2-Fc | 36.12 |
| TWEAKR-Fc | 36.17 |
| TNFR2-TWEAKR fusion protein | 12.73 |

EXPERIMENTAL EXAMPLE 2

Measurement of Binding Affinity Between TNFR2-TWEAKR Fusion Protein and Ligand Thereof To investigate antagonism between TNFR2-Fc, TWEAKR-Fc, and TNFR2-TWEAKR fusion protein constructed above and their ligands TNF-α and TWEAK, binding affinity test was performed.

Each well of the ELISA plate (#439454, Nunc, Denmark) was coated with 100 μl of PBS (pH7.4) containing 100 ng of TNF-α (#C001-1 MG, enzynomics, Korea) or TWEAK at 4° C. for overnight. Upon completion of coating, 200 μl of PBS containing 4% skim milk (#232100, Difco, France) was added to each well of the ELISA plate, followed by blocking with blocking buffer (4% skim milk in PBS) at room temperature for about 1 hour, in order to inhibit non-specific reaction. Upon completion of blocking, the blocking buffer was eliminated from the ELISA plate. Each purified protein was added to 100 μl of blocking buffer at the concentration of 100 nM, followed by serial dilution (¼ dilutions). Then, reaction was induced at room temperature for approximately 2 hours. Next, the plate was washed with 200 μl of PBS five times. 2 μl of anti-Human Fc-HRP (#31413, Thermo, USA), the secondary antibody, was added to 4 ml of PBS supplemented with 1% skim milk, which was distributed to each well of ELISA plate (200 μl/well), followed by reaction at room temperature for 1 hour. Upon completion of the reaction, the secondary antibody was eliminated from the ELISA plate, followed by washing with 200 μl of PBS five times. 100 μl of reaction mixture prepared by mixing 10 μl of hydrogen peroxide solution ($H_2O_2$, #H1009-100ML, Sigma, USA), 10 μl of PC buffer [5.1 g Citric acid monohydrate, 7.3 g Sodium phosphate (pH 5.0)/l], and 1 OPD tablet (#P8787-100TAB Sigma USA) was added to each well of the plate, followed by reaction at room temperature for 10 minutes at dark place. After confirming color development, the reaction was terminated by adding STOP buffer (50 μl/well). Kd value was measured at 490 nm by using ELISA reader.

As a result, as shown in Table 5, TNF-α ligand demonstrated high binding affinity to TNFR2-Fc and TNFR2-TWEAKR-Fc. In the meantime, the ligand showed low binding affinity to TWEAKR-Fc. TWEAK ligand demonstrated low Kd value against TWEAKR-Fc and TNFR2-TWEAKR fusion protein, suggesting that the ligand had high binding affinity to them. In the meantime, TWEAK ligand showed low binding affinity to TNFR2-Fc (Table 5 and FIG. 10).

TABLE 5

| Sample | TNF-α (Kd value) | TWEAK (Kd value) |
| --- | --- | --- |
| TNFR2-Fc | 1.080 | 37.89 |
| TWEAKR-Fc | 46.13 | 0.6414 |
| TNFR2-TWEAKR fusion protein | 1.724 | 0.1217 |

EXPERIMENTAL EXAMPLE 3

Cytokine Expression in Synovial Membrane Tissue

Immunohistochemical staining was performed to investigate the expressions of TWEAK, TWEAKR (TWEAK receptor), the inflammatory cytokine IL-17, and RANKL (receptor activator of nuclear factor kappa B ligand) playing an important role in osteoclast in synovial membrane tissues obtained from autoimmune disease patients treated with bone replacement. To fix the structure of synovial membrane tissues obtained from autoimmune disease patients, 4% paraformaldehyde was used. The tissues were embedded in paraffin according to the conventional method. The paraffin embedded tissues were made into 7 μm thick sections, which were placed on slide. Deparaffination was performed by using xylene, during which dehydration was also performed with ethanol. Endogenous peroxidase was blocked with 3% hydrogen peroxide ($H_2O_2$), followed by washing with PBS (phosphate-buffered saline, Gibco BRL, Carlsbad, Calif., USA). To block non-specific reaction, the slide was reacted with 100 μl of blocking solution (10% normal goat serum) for 30 minutes. Then, primary antibodies TWEAK, TWEAKR, IL-17, and RNAKL (Santa Cruz, Burlingame, Calif., USA) were diluted at the ratio of 1:100, which were added to the tissue by 100 μl each, followed by reaction at 4° C. for 16~18 hours. Upon completion of the reaction with the primary antibodies, unattached antibodies were eliminated, followed by washing with 50 ml of PBS. The tissue was then reacted with 100 μl of biotin-conjugated secondary antibody and peroxidase-conjugated streptavidin. Color development was induced with DAB, followed by observation under optical microscope (Tokyo, Japan).

OA patient tissue was stained and used as the control. The expressions of TWEAK and TWEAKR were significantly higher in the tissue of autoimmune arthritis patient than in the tissue of OA patient. The expressions of IL-17 and RANKL were also higher in the tissue of autoimmune arthritis patient (FIG. 11).

EXPERIMENTAL EXAMPLE 4

Inhibition of Inflammatory Cytokine by TNFR2-TWEAKR Fusion Protein

<4-1> Separation of Peripheral Blood Mononuclear Cells

Blood was obtained from healthy people by using heparin treated syringe, which was then diluted with PBS at the ratio of 1:1. Ficoll (Amercham Biosciences, Burkinghamshire, England) was added to the diluted blood at the ratio of 1:4, with making blood float on the top of Ficoll layer, followed by centrifugation at 2000 rpm at 20r for 30 minutes. Peripheral blood mononuclear cells (PBMCs) were separated from buffy coat. The separated cells were washed with PBS, and then diluted in RPMI 1640 (Gibco BRL) supplemented with 10% fetal bovine serum (Gibco, Burlingame, Calif., USA) at the density of $1 \times 10^6$ cells/ml.

<4-2> Th17 Cell Culture

The PBMCs obtained in Experimental Example <4-1> were diluted in RPMI 1640 supplemented with 10% FBS at the density of $5 \times 10^5$ cells/500 μl, which was distributed in each well of 48 well plate (Nalgen Nunc International, IL, USA). TNFR2-Fc, TWEAKR-Fc, and TNFR2-TWEAKR fusion protein were treated thereto at the concentration of 10 μg/ml, followed by culture for 1 hour. 1 hour later, the cells deposited on the floor were harvested up by using pipette, which were then transferred in 48 well plate coated with anti-CD3 (BD Pharmingen, San Diego, Calif., USA) at the concentration of 0.3 μg/ml. To induce differentiation of the PBMCs into Th17 cells, IL-6 (R&D Systems, Minneapolis, Minn., USA; 20 ng/ml), IL-23 (R&D Systems; 10 ng/ml), and IL-1β (R&D Systems; 5 ng/ml) were treated thereto, followed by culture in a 37° C., 5% $CO_2$ incubator. For 72 hours, the medium was not changed and additional stimulation was avoided.

<4-3> RT-PCR

Total RNA was extracted from the cells cultured for 72 hours in Experimental Example <4-2> by using RNA zol-B (Molecular Research Center, Cincinnati, Ohio, USA). 1 μl of random primer (Genotech, Daejeon, Korea) was added to the total 2 μg RNA (3 μl), which stood at 70° C. for 5 minutes, followed by quick-freezing in ice. The RNA-primer mixture was mixed with 4 μl of 5×M-MULV buffer, 1 μl of 10 mM dNTP, and 0.5 μl of RNase inhibitor (Takara, Shiga, Japan), to which 9.5 μl of distilled water was added to make the total volume of the reaction solution 19 μl. Reaction was induced at 25r for 5 minutes, and then 1 μl of reverse transcriptase M-MULV (Takara, Shiga, Japan) was treated thereto. Reaction was induced stepwise at 25° C. for 5 minutes, at 42° C. for 60 minutes, and then at 72° C. for 10 minutes to obtain cDNA.

RT-PCR was performed by using the cDNA produced above as a template. The total volume of RT-PCR reaction mixture for each sample was 25 μl [2.5 μl of 10× reaction buffer, 2.5 μl of 0.5 mM dNTP, 0.3 μl of Taq (Takara, Shing a, Japan), 2 μl of each primer (forward primer, reverse primer), 1 μl of cDNA, and 14.7 μl of distilled water]. Dual-bay thermal cycler system (MJ Research) was used for the amplification. Instead of cDNA extracted, distilled water was used for the negative control. PCR was confirmed to be free from contamination by using the negative control which did not give any PCR product.

PCR for the amplification of IL-21 was performed as follows; predenaturation at 94° C. for 3 minutes, denaturation at 94° C. for 30 seconds, annealing at 56° C. for 30 seconds, polymerization at 72° C. for 30 seconds, 30 cycles from denaturation to polymerization, and final extension at 72° C. for 7 minutes. PCR for the amplification of IL-17 was performed as follows; predenaturation at 94° C. for 3 minutes, denaturation at 94° C. for 1 minute, annealing at 56° C. for 1 minute, polymerization at 72° C. for 1 minute, 30 cycles from denaturation to polymerization, and final extension at 72° C. for 7 minutes. PCR for the amplification of RORc and β-actin was performed as follows; predenaturation at 94° C. for 3 minutes, denaturation at 94° C. for 30 seconds, annealing at 60° C. for 30 seconds, polymerization at 72° C. for 30 seconds, 30 cycles or 26 cycles from denaturation to polymerization. The amplified products obtained by PCR proceeded to electrophoresis on 1.5% agarose gel containing ethidium bromide and images were obtained by using Gel-Doc 2000 (Bio-rad Laboratories, Hercules, Calif.). The amplified products were quantified by concentration measurement technique using Quantity-One program (Bio-rad). The obtained values were converted into the ratios to β-actin and then mRNA expressions among cell groups were compared. The primer sequences used herein are as follows:

```
IL-21;
                                    (SEQ. ID. NO: 12)
    5'-CTT ACC TGG CAA GAC CAG TAT GA-3';

(SEQ. ID. NO: 13)
    5'-GTA GAA GGC AGG GTC TTC GTA AT-3';

IL-17;
                                    (SEQ. ID. NO: 14)
    5'-TGA AGT GCT GTC TGG AGC AG-3';, (SEQ. ID. NO: 15)
    5'-TCC TCA GAA TCA TCC ATG TC-3';

RORc;
                                    (SEQ. ID. NO: 16)
    5'-AGT CGG AAG GCA AGA TCA GA-3';

(SEQ. ID. NO: 17)
    5'-CAA GAG AGG TTC TGG GCA AG-3';

β-actin;
                                    (SEQ. ID. NO: 18)
    5'-GGA CTT CGA GCA AGA GAT GG-3';
and
                                    (SEQ. ID. NO: 19)
    5'-TGT GTT GGC GTA CAG GTC TTT G-3'.
```

The obtained values were converted into the ratios to β-actin and then mRNA expressions among cell groups were compared.

As a result, in the differentiated Th17 cells, the mRNA expressions of the inflammatory cytokines IL-17 and IL-21, and the expression of mRNA of the specific transcription factor RORc, which has been reported to be expressed in the Th17-polarizing condition, were very high. However, when Th17 cells were treated with 10 μg of TNFR2-TWEAKR fusion protein, the expressions of IL-17, IL-21, and RORc were significantly suppressed (FIG. 12).

<4-4> Decrease of IL-17 Production by TNFR2-TWEAKR Fusion Protein

To confirm the down-regulation of IL-17 by TNFR2-TWEAKR fusion protein, inflammatory cytokine IL-17 in the supernatant obtained from Th17 cell culture medium treated with TNFR2-TWEAKR fusion protein in Experimental Example <2-3> was quantified by ELISA.

IL-17 antibody (R&D Systems) was added in 96 well plate for sandwich ELISA at the concentration of 2 μg/ml (100 μl/well), followed by reaction at room temperature for 2 hours. 200 μl of blocking buffer prepared by mixing 1% BSA with 0.05% PBST was added thereto, followed by reaction at room temperature for 2 hours. Human recombinant IL-17 (R&D Systems) to be used as a standard was serially diluted at 5,000~78.125 pg/ml. 100 μl of the diluted IL-17 was added to each well. The supernatant of cell culture medium to be measured along with the standard was added to each well (50 μl/well), followed by reaction at room temperature for 2 hours. Upon completion of the reaction, each well of the plate was washed with 300 μl of 0.05% PBST four times. Biotin-conjugated anti-human IL-17 (R&D Systems) was diluted at the concentration of 200 ng/ml, which was distributed to each well by 50 μl/well, followed by reaction at room temperature for 2 hours. Upon completion of the reaction, the plate was washed with PBST 4 times. ExtraAvidin-Alkaline Phosphatase conjugate (Sigma, Louis, Mo., USA) was diluted (1:2000), which was distributed to each well by 50 μl/well, followed by reaction at room temperature for 2 hours. After washing the plate with PBST, 50 μl of phosphate disodium salt hexahydrate (PNPP)/DEA solution (1 mg/ml) was added to each well of the plate for further reaction. Upon completion of the reaction, 50 µl of 0.2 N NaOH was added thereto to terminate the reaction and then $OD_{405}$ was measured.

As a result, production of the inflammatory cytokine IL-17 was increased when Th17 cells were being differentiated. When the cells were treated with TNFR2-Fc and TWEAKR-Fc at the concentration of 10 µg/g, IL-17 production was significantly reduced compared with other cell group treated with TNFR2-TWEAKR fusion protein (FIG. 12).

EXPERIMENTAL EXAMPLE 5

Measurement of IL-10 Production Induced by TNFR2-TWEAKR Fusion Protein

To investigate whether or not TNFR2-TWEAKR fusion protein could increase the function of Treg, the immune suppressive cells that keeps balance with autoantigens to protect from autoimmunity while it suppresses Th17 cell response, the anti-inflammatory cytokine IL-10 generated in Treg cells was quantified by ELISA.

IL-10 antibody (R&D Systems) was added to 96 well plate for sandwich ELISA at the concentration of 2 µg/ml (100 µl/well), followed by reaction at room temperature for 2 hours. 200 µl of blocking buffer prepared by mixing 1% BSA with 0.05% PBST was added thereto, followed by reaction at room temperature for 2 hours. Human recombinant IL-10 (R&D Systems) to be used as a standard was serially diluted at 5,000~78.125 pg/ml, which was distributed to each well by 100 µl/well. The supernatant of cell culture medium to be measured along with the standard was added to each well (100 µl/well), followed by reaction at room temperature for 2 hours. Upon completion of the reaction, each well of the plate was washed with 300 µl of 0.05% PBST four times. Biotin-conjugated anti-human IL-10 (R&D Systems) was diluted at the concentration of 200 ng/ml, which was distributed to each well by 50 µl/well, followed by reaction at room temperature for 2 hours. Upon completion of the reaction, the plate was washed with PBST 4 times. ExtraAvidin-Alkaline Phosphatase conjugate (Sigma, Louis, Mo., USA) was diluted at the concentration of 1:2000, which was distributed to each well by 100 µl/well, followed by reaction at room temperature for 2 hours. After washing the plate with PBST, 100 µl of phosphate disodium salt hexahydrate (PNPP)/DEA solution (1 mg/ml) was added to each well of the plate for further reaction. Upon completion of the reaction, 100 µl of 0.2 N NaOH was added thereto to terminate the reaction and then $OD_{405}$ was measured.

As a result, IL-10 production was significantly increased when TNFR2-TWEAKR fusion protein was treated into Th17-polarizing condition, compared with when TNFR2-Fc or TWEAKR-Fc was treated (FIG. 13).

EXPERIMENTAL EXAMPLE 6

Correlation Between TWEAK and RANKL

Bone destruction, one of major symptoms of autoimmune arthritis, is caused when bone erosion gets serious due to the excessive generation of osteoclasts. The major cause of osteoclast differentiation is RNAKL, which allegedly is up-regulated by the cytokine such as TNF and IL-1. To investigate the correlation between TWEAK and RANKL, TWEAK and RANKL levels in serum and synovial fluid of autoimmune arthritis patient were measured by ELISA.

The quantification of TWEAK and RANKL in serum and synovial fluid was performed by using the product of Peprotech Co. 100 µg/ml of RANKL capture antibody was diluted with PBS to make the concentration 1 µg/ml, which was loaded in ELISA plate (100 µl/well), followed by reaction at room temperature for 12 hours. The diluted capture antibody solution was eliminated, followed by washing with 300 µl of washing buffer (0.05% Tween-20 in PBS) four times. After washing, 300 µl of blocking buffer (1% BSA in PBS) was loaded in each well, followed by reaction at room temperature for 1 hour. One hour later, the plate was washed with 300 µl of washing buffer four times. 1 µg/ml of RANKL protein was diluted in dilution buffer (0.05% Tween-20, 0.1% BSA in PBS) at the concentration of 2 ng/ml, which would be used as a standard, which was serially diluted by 5% until the concentration reached 0 ng/ml. The sample and the prepared standard were distributed in ELISA plate (100 µl/well), followed by reaction at room temperature for 2 hours. Upon completion of the reaction, the plate was washed four times. 100 µg/µl of detecting antibody was diluted in dilution buffer at the concentration of 0.5 µg/ml, which was loaded to each well by 100 µl, followed by reaction at room temperature for 2 hours. After washing the plate 4 times, 5.5 µl of avidin-HRP conjugate was mixed with 11 ml of dilution buffer (1:2000). The diluted solution was distributed to each well by 100 µl, followed by reaction at room temperature for 2 hours. Upon completion of the reaction, the plate was washed 4 times. 1 mg/ml of phosphate disodium salt hezahydrate (PNPP)/DEA solution was added to the plate (100 µl/well), followed by reaction. Upon completion of the reaction, 100 µl of 0.2 N NaOH was added thereto to terminate the reaction and then $OD_{405}$ was measured.

For the quantification of TWEAK, 100 µg/ml of capture antibody was diluted with PBS at the concentration of 0.5 µg/ml, which was loaded in ELISA plate (100 µl/well), followed by reaction at room temperature for 12 hours. The diluted capture antibody solution was eliminated, followed by washing with 300 µl of washing buffer four times. After washing, 300 µl of blocking buffer was added to each well, followed by reaction at room temperature for 1 hour. One hour later, the plate was washed with 300 µl of washing buffer four times. 1 µg/ml of RANKL protein was diluted in dilution buffer at the concentration of 2 ng/ml, which would be used as a standard, which was serially diluted by 5% until the concentration reached 0 ng/ml. The sample and the prepared standard were distributed in ELISA plate (100 µl/well), followed by reaction at room temperature for 2 hours. Upon completion of the reaction, the plate was washed four times. 100 µg/ml of detecting antibody was diluted in dilution buffer at the concentration of 0.5 µg/ml, which was loaded to each well by 100 µl, followed by reaction at room temperature for 2 hours. After washing the plate 4 times, 5.5 µl of avidin-HRP conjugate was mixed with 11 ml of dilution buffer (1:2000). The diluted solution was distributed to each well by 100 µl, followed by reaction at room temperature for 30 minutes. Upon completion of the reaction, the plate was washed 4 times. 1 mg/ml of phosphate disodium salt hezahydrate (PNPP)/DEA solution was added to the plate (100 µl/well), followed by reaction. Upon completion of the reaction, 100 µl of 0.2 N NaOH was added thereto to terminate the reaction and then $OD_{405}$ was measured.

As a result, it was confirmed that TWEAK and RANKL levels in serum and synovial fluid of autoimmune arthritis patient were closely correlated with each other, consistently with the result shown in the histostaining test of Experimental Example 1 (FIG. 14). It was thereby suggested that simultaneous inhibition of both TNF and TWEAK, known to increase RANKL by using TNFR2-TWEAKR fusion protein, could increase the treatment effect.

EXPERIMENTAL EXAMPLE 7

Treatment Effect of TNFR2-TWEAKR Fusion Protein on Arthritis in CIA Mouse Model

To investigate the treatment effect of the TNFR2-TWEAKR fusion protein of the present invention on arthritis, CIA (collagen induced arthritis) mouse model was treated with TNFR2-TWEAKR fusion protein. Then, treatment effect was investigated.

Particularly, to induce CIA, male DBA/1J mice (Orient-Bio, Korea) at 6 weeks were injected at the tail with 100 μg of type II collagen (CII) mixed with same amount of complete Freund's adjuvant (CFA), leading to the primary immunization. Each experimental group had 6 mice. From a week (7 days) after the immunization, the mice were administered with 50 μg of TWEAKR/TNFR2-Fc (TNFR2-TWEAKR fusion protein) and 100 μg of Enbrel by intraperitoneal injection (I.P.) three times per week for three weeks (9 times total). Three investigators observed joint inflammation three times a week starting from the primary immunization. Evaluation was performed by mean arthritic index as follows; points are given grade by grade; points given are all added up and divided by 4 to give mean value; means obtained from three different investigators for each mouse are added, from which average was obtained. One leg was given 25%, based on which the number of the swollen legs was calculated, resulting in incidence:

0 point: none of edema or swelling;
1 point: light edema and redness limited in foot or ankle joint;
2 points: light edema and redness over metatarsal from ankle joint;
3 points: severe edema and redness over metatarsal from ankle joint; and
4 points: edema and redness all over the leg from ankle.

As a result, as shown in FIG. 15, it was confirmed by observing clinical score and incidence that excellent arthritis treatment effect was demonstrated in the CIA mouse model group treated with the TNFR2-TWEAKR fusion protein of the present invention. Such treatment effect was greater than that observed in the positive control group treated with Enbrel, the conventional arthritis treatment agent (FIG. 15).

EXPERIMENTAL EXAMPLE 8

Confirmation of Alleviation Effect of TNFR2-TWEAKR Fusion Protein on Arthritis in CIA Mouse Model by Immunohistochemical Staining Joints were extracted from the experimental CIA mouse model groups treated with TNFR2-TWEAKR fusion protein and Enbrel of Experimental Example 7. Immunohistochemical staining was performed to investigate infiltration and inflammation in joint and cartilage destruction.

Particularly, to perform immunohistochemical staining, joints were taken from CIA mice respectively treated with TNFR2-TWEAKR fusion protein and Enbrel. Then, the joints were fixed in 10% neutral buffered formalin and bones were decalcified by using EDTA. The joint tissues were embedded in paraffin. The paraffin embedded joint tissues were made into 7 μm thick sections, which were placed on slide. Before staining, deparaffination was performed by using xylene, during which dehydration was also performed with ethanol (high conc.→low conc.). Then haematoxylin and eosin staining was performed. Cartilage destruction and inflammation were measured by using Safranin O and Toluidine blue method that is able to detect proteoglycans included in cartilage.

As a result, as shown in FIG. 16, cellular infiltration was remarkably reduced when CIA mouse model was treated with TNFR2-TWEAKR fusion protein, compared with when nothing was treated. It was also observed by using Safranin O and Toluidine blue method that inflammation and destruction of cartilage were alleviated when TNFR2-TWEAKR fusion protein was treated (FIG. 16).

EXPERIMENTAL EXAMPLE 9

Confirmation of Alleviation Effect of TNFR2-TWEAKR Fusion Protein on Inflammation in CIA Mouse Model by Immunohistochemical Staining Joints were extracted from the experimental CIA mouse model groups treated with TNFR2-TWEAKR fusion protein and Enbrel of Experimental Example 7. Immunohistochemical staining was performed to investigate the expressions of inflammatory factors.

Particularly, joints were taken from CIA mice respectively treated with TNFR2-TWEAKR fusion protein and Enbrel. Then, the joints were fixed in 10% neutral buffered formalin and bones were decalcified by using EDTA. The joint tissues were embedded in paraffin. The paraffin embedded joint tissues were made into 7 μm thick sections, which were placed on slide. Before staining, deparaffination was performed by using xylene, during which dehydration was also performed with ethanol (high conc.→low conc.). The inflammatory cytokines IL-17, TNF-α, IL-1β, and IL-6, and Receptor activator of nuclear factor-κB (RANK), and Vascular endothelial growth factor (VEGF) were stained by the method of immunohistochemical staining, followed by observation under optical microscope.

As a result, as shown in FIG. 17, the expressions of the inflammatory cytokines IL-17, TNF-α, IL-1β, and IL-6 were all decreased in the group treated with the TNFR2-TWEAKR fusion protein of the present invention, compared with the other CIA mouse model groups not treated with the fusion protein. Besides, the expressions of VEGF, the important factor for angiogenesis, and RANK that is the factor showing osteoclast differentiation were hardly observed. Such expression patterns of inflammatory cytokines, VEGF, and RANK in the group treated with TNFR2-TWEAKR fusion protein were consistent with the aspect of the group treated with Enbrel, suggesting that the TNFR2-TWEAKR fusion protein of the present invention can also be effectively used for the treatment of arthritis (FIG. 17).

EXPERIMENTAL EXAMPLE 10

CII Specific IgG2a Production in CIA Mouse Model

The CIA mouse model used in Experimental Example 7 was immunized by one time injection of type II Collagen (CII). Then, the TNFR2-TWEAKR fusion protein of the present invention was administered to the animal three times a week for three weeks (9 times total). Blood CII was measured during the administration period.

100 μg of CII mixed with the same amount of complete Freund's adjuvant (CFA) was injected into the tails of DAB mice. One week later, the TNFR2-TWEAKR fusion protein of the present invention was administered to the mice 9 times in total for three weeks. Blood was taken from the eyes of the mice before the administration of TNFR2-TWEAKR fusion protein (0), after the first administration, after the $6^{th}$ administration, and within 6-12 hours after the last administration, to obtain serum. To measure the amount of CII-specific IgG2a, CII antibody was diluted at the ratio of 1:1,000, with which 96-well plate was coated, followed by reaction for 2 hours. After eliminating the coating buffer, 200 μl of blocking buffer was added to each well, followed by reaction at room temperature for 1 hour. Then, serum of experimental group or control group was diluted, which was added thereto (50 μl/well), followed by reaction at room temperature for 1 hour. After washing the plate with IgG washing buffer 5 times, anti-mouse IgG HRP (1:75,000) was added thereto (50 μl/well), followed by reaction at room temperature for 1 hour. Upon completion of the reaction, the plate was washed with IgG washing buffer 5 times, followed by reaction with TMB substrate solution. Color development was stopped by using 1N $H_2SO_4$, and then $OD_{450}$ was measured with ELISA reader.

As a result, as shown in FIG. 18, the amount of CII-specific IgG2a was not changed over the time in CIA mouse model group not treated with any Fc fusion protein. However, in the group treated with TNFR2-TWEAKR fusion protein, the amount of CII-specific IgG2a was decreased over the administration times. In addition, in the group treated with Enbrel, OD value seemed to be slightly increased after the first administration, but began to decrease after the additional Enbrel administration (FIG. 18).

EXPERIMENTAL EXAMPLE 11

Measurement of Th17 and Treg Cells Expressions in Spleen of CIA Mouse Model

To investigate the effect of the TNFR2-TWEAKR fusion protein of the present invention on the expressions of Th17 and Treg cells in CIA mouse model, spleen tissues were extracted from the mice used in Experimental Example 7. Then, Th17 (CD4+IL-17+) and Treg (CD4+CD25+Foxp3+) cells were observed by confocal microscopy of immunostaining.

Particularly, spleen was extracted from the CIA mouse model used in Experimental Example 7, which was embedded with OCT compound. The tissues were quick-frozen by using liquid nitrogen, which were sliced into 7 μm sections by using cryotome and then placed on slide. The section placed on the slide was fixed with acetone and non-specific reaction was blocked by using 10% normal goat serum for 30 minutes. Staining of the Treg markers, CD4, CD25, and Foxp3, was performed by using PE-labeled anti-CD4 antibody, Allophycocyanin-labeled anti-CD25 antibody (Biolegend), and FITC-labeled anti-Foxp3 Ab antibody. Staining of the Th17 markers, CD4, and IL-17, was performed by using biotinylated anti-CD4 antibody (BD Biosciences), and PE-labeled anti-IL-17 antibody. The said antibodies were diluted in PBS (pH 7.5) at the ratio of 1:100, followed by reaction with the tissues placed on the slide at 4° C. for overnight. On the next day, the tissues reacted with biotinylated anti-CD4 antibody were additionally reacted with streptavidin cy-3 at room temperature for 2 hours. After washing the slide with PBS three times, the stained tissues were observed under confocal microscope (LSM 510 Meta. Zeiss, Gottingen, Germany).

As a result, as shown in FIG. 19, in the spleen tissues obtained from the CIA mouse model treated with the TNFR2-TWEAKR fusion protein of the present invention, the number of Foxp3+ cells was increased, compared with the CIA mouse model treated with nothing. In the meantime, the expression of Th17 (CD4+IL-17+) was reduced in the group treated with TNFR2-TWEAKR fusion protein or Enbrel, compared with the CIA mouse model treated with nothing (FIG. 19).

The Manufacturing Examples of the composition of the present invention are described hereinafter.

MANUFACTURING EXAMPLE 1

Preparation of Pharmaceutical Formulations

<1-1> Preparation of Powders

| | |
|---|---|
| TNFR2-TWEAKR fusion protein | 2 g |
| Lactose | 1 g |

Powders were prepared by mixing all the above components, which were filled in airtight packs according to the conventional method for preparing powders.

<1-2> Preparation of Tablets

| | |
|---|---|
| TNFR2-TWEAKR fusion protein | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| TNFR2-TWEAKR fusion protein | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| | |
|---|---|
| TNFR2-TWEAKR fusion protein | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| | |
|---|---|
| TNFR2-TWEAKR fusion protein | 150 mg |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

Industrial Applicability

As explained herein before, the TNFR2-TWEAKR fusion protein of the present invention reduces the secretion of the inflammatory cytokine IL-17 but increases the secretion of the anti-inflammatory cytokine IL-10. Such effect of the TNFR2-TWEAKR fusion protein of the present invention is greater than that of TNFR2-Fc or TWEAKR-Fc. The expressions of RANKL and TWEAK in synovial membrane of autoimmune arthritis patient are increase correlatively. When the TNFR2-TWEAKR fusion protein of the present invention was administered to CIA (collagen induced Arthritis) animal model, it inhibited infiltration and inflammation in joint, reduced the destruction of cartilage, increased the expression of Tregs, the immune suppressive cells, and demonstrated treatment effect on autoimmune rheumatoid arthritis. Therefore, the TNFR2-TWEAKR fusion protein of the present invention can be effectively used as an active ingredient for the composition for the prevention and treatment of autoimmune disease.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for the treatment of autoimmune disease comprising administering a pharmaceutically effective dose of a fusion protein to a subject with autoimmune disease, wherein the fusion protein comprises the full sequence of a TNFR2 (tumor necrosis factor receptor type 2) protein fused to the full sequence of a TWEAKR (TNF-related weak inducer of apoptosis receptor) protein.

2. The method according to claim 1, wherein the autoimmune disease is selected from the group consisting of pernicious anemia, type 1 diabetes, autoimmune arthritis, lupus, multiple sclerosis, reactive arthritis, and dermatomyositis.

* * * * *

SEQUENCE LISTING

```
<160> NUMBER OF SEQ ID NOS: 19

<210> SEQ ID NO 1
<211> LENGTH: 228
<212> TYPE: PRT
<213> ORGANISM: Artificial Sequence
<220> FEATURE:
<223> OTHER INFORMATION: TNF receptor alpha 2 and TWEAKR fusion protein

<400> SEQUENCE: 1

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Glu Gln Ala Pro Gly Thr Ala Pro Cys Ser Arg Gly Ser
            180                 185                 190

Ser Trp Ser Ala Asp Leu Asp Lys Cys Met Asp Cys Ala Ser Cys Arg
        195                 200                 205

Ala Arg Pro His Ser Asp Phe Cys Leu Gly Cys Ala Ala Ala Pro Pro
    210                 215                 220

Ala Pro Phe Arg
225

<210> SEQ ID NO 2
<211> LENGTH: 230
<212> TYPE: PRT
<213> ORGANISM: Homo sapiens
```

```
<400> SEQUENCE: 2

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu
225                 230

<210> SEQ ID NO 3
<211> LENGTH: 49
<212> TYPE: PRT
<213> ORGANISM: Homo sapiens

<400> SEQUENCE: 3

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Pro Pro Ala Pro Phe
        35                  40                  45

Arg

<210> SEQ ID NO 4
<211> LENGTH: 38
<212> TYPE: DNA
<213> ORGANISM: Artificial Sequence
<220> FEATURE:
<223> OTHER INFORMATION: TWEAKR F228 forward primer

<400> SEQUENCE: 4 caggggggccg tgggggccga gcaagcgcca ggcaccgc                          38
```

-continued

```
<210> SEQ ID NO 5
<211> LENGTH: 39
<212> TYPE: DNA
<213> ORGANISM: Artificial Sequence
<220> FEATURE:
<223> OTHER INFORMATION: TWEAKR F228 reward primer

<400> SEQUENCE: 5
tagcggccga cgcggccaat tcagctgggg ggctggggc                              39

<210> SEQ ID NO 6
<211> LENGTH: 38
<212> TYPE: DNA
<213> ORGANISM: Artificial Sequence
<220> FEATURE:
<223> OTHER INFORMATION: TWEAKR F448 forward primer

<400> SEQUENCE: 6 caggggggccg tgggggccag tttggggagc cgggcatc                               38

<210> SEQ ID NO 7
<211> LENGTH: 39
<212> TYPE: DNA
<213> ORGANISM: Artificial Sequence
<220> FEATURE:
<223> OTHER INFORMATION: TWEAKR F448 reward primer

<400> SEQUENCE: 7
tagcggccga cgcggccaag tgaacctgga agagtccga                              39

<210> SEQ ID NO 8
<211> LENGTH: 38
<212> TYPE: DNA
<213> ORGANISM: Artificial Sequence
<220> FEATURE:
<223> OTHER INFORMATION: TNFR2 F227 forward primer

<400> SEQUENCE: 8 caggggggccg tgggggcctt gcccgcccag gtggcatt                               38

<210> SEQ ID NO 9
<211> LENGTH: 39
<212> TYPE: DNA
<213> ORGANISM: Artificial Sequence
<220> FEATURE:
<223> OTHER INFORMATION: TNFR2 F227 reward primer

<400> SEQUENCE: 9
tagcggccga cgcggccaat tcagctgggg ggctggggc                              39

<210> SEQ ID NO 10
<211> LENGTH: 41
<212> TYPE: DNA
<213> ORGANISM: Artificial Sequence
<220> FEATURE:
<223> OTHER INFORMATION: Reward primer for TNFR2-TWEAKR fusion protein

<400> SEQUENCE: 10
gcggtgcctg gcgcttgctc cgtgcagact gcatccatgc t                           41

<210> SEQ ID NO 11
<211> LENGTH: 41
<212> TYPE: DNA
<213> ORGANISM: Artificial Sequence
<220> FEATURE:
<223> OTHER INFORMATION: Forward primer for TNFR2-TWEAKR fusion protein
```

<400> SEQUENCE: 11
agcatggatg cagtctgcac ggagcaagcg ccaggcaccg c     41

<210> SEQ ID NO 12
<211> LENGTH: 23
<212> TYPE: DNA
<213> ORGANISM: Artificial Sequence
<220> FEATURE:
<223> OTHER INFORMATION: IL-21 forward primer

<400> SEQUENCE: 12
cttacctggc aagaccagta tga     23

<210> SEQ ID NO 13
<211> LENGTH: 23
<212> TYPE: DNA
<213> ORGANISM: Artificial Sequence
<220> FEATURE:
<223> OTHER INFORMATION: IL-21 reward primer

<400> SEQUENCE: 13
gtagaaggca gggtcttcgt aat     23

<210> SEQ ID NO 14
<211> LENGTH: 20
<212> TYPE: DNA
<213> ORGANISM: Artificial Sequence
<220> FEATURE:
<223> OTHER INFORMATION: IL-17 forward primer

<400> SEQUENCE: 14
tgaagtgctg tctggagcag     20

<210> SEQ ID NO 15
<211> LENGTH: 20
<212> TYPE: DNA
<213> ORGANISM: Artificial Sequence
<220> FEATURE:
<223> OTHER INFORMATION: IL-17 reward primer

<400> SEQUENCE: 15
tcctcagaat catccatgtc     20

<210> SEQ ID NO 16
<211> LENGTH: 20
<212> TYPE: DNA
<213> ORGANISM: Artificial Sequence
<220> FEATURE:
<223> OTHER INFORMATION: RORc forward primer

<400> SEQUENCE: 16
agtcggaagg caagatcaga     20

<210> SEQ ID NO 17
<211> LENGTH: 20
<212> TYPE: DNA
<213> ORGANISM: Artificial Sequence
<220> FEATURE:
<223> OTHER INFORMATION: RORc reward primer

<400> SEQUENCE: 17
caagagaggt tctgggcaag     20

<210> SEQ ID NO 18
<211> LENGTH: 20

-continued

```
<212> TYPE: DNA
<213> ORGANISM: Artificial Sequence
<220> FEATURE:
<223> OTHER INFORMATION: beta actin forward primer

<400> SEQUENCE: 18
ggacttcgag caagagatgg                                               20

<210> SEQ ID NO 19
<211> LENGTH: 22
<212> TYPE: DNA
<213> ORGANISM: Artificial Sequence
<220> FEATURE:
<223> OTHER INFORMATION: beta actin reward primer

<400> SEQUENCE: 19
tgtgttggcg tacaggtctt tg                                            22
```